US010201649B2

(12) United States Patent
Haag et al.

(10) Patent No.: US 10,201,649 B2
(45) Date of Patent: Feb. 12, 2019

(54) CARBON DIOXIDE REMOVAL SYSTEM

(71) Applicant: MAQUET CARDIOPULMONARY GmbH, Rastatt (DE)

(72) Inventors: Ulrich Haag, Bisingen (DE); Oliver Möllenberg, Rastatt (DE); Ralf Thölke, Rastatt (DE); Mathias Nakel, Rastatt (DE); Rudolf Kober, Rastatt (DE)

(73) Assignee: MAQUET CARDIOPULMONARY GmbH, Rastatt (DE)

( * ) Notice: Subject to any disclaimer, the term of this patent is extended or adjusted under 35 U.S.C. 154(b) by 0 days.

(21) Appl. No.: 14/854,926

(22) Filed: Sep. 15, 2015

(65) Prior Publication Data

US 2016/0000989 A1 Jan. 7, 2016
US 2018/0236158 A9 Aug. 23, 2018

Related U.S. Application Data

(63) Continuation-in-part of application No. PCT/IB2014/001600, filed on Mar. 14, 2014.

(Continued)

(30) Foreign Application Priority Data

May 16, 2013 (EP) .................................... 13168103

(51) Int. Cl.
*B01D 19/00* (2006.01)
*B01D 63/02* (2006.01)
(Continued)

(52) U.S. Cl.
CPC ........ *A61M 1/3627* (2013.01); *A61M 1/1698* (2013.01); *A61M 1/3666* (2013.01);
(Continued)

(58) Field of Classification Search
CPC .. B01D 19/0031; B01D 63/02; B01D 63/026; B01D 2325/02; A61M 1/1698; A61M 1/3627; A61M 1/3666; A61M 2230/30
See application file for complete search history.

(56) References Cited

U.S. PATENT DOCUMENTS 3,890,969 A 6/1975 Fischel
4,620,965 A * 11/1986 Fukusawa ........... A61M 1/1698 210/321.8

(Continued)

FOREIGN PATENT DOCUMENTS

CA 1086594 A 9/1980
DE 200 11 060 U1 9/2000

(Continued)

OTHER PUBLICATIONS

Search Report and Written Opinion for International Application No. PCT/IB2014/001600, dated Mar. 3, 2015.

(Continued)

*Primary Examiner* — Jason M Greene
(74) *Attorney, Agent, or Firm* — Wesley Scott Ashton; Kevin T. Godlewski

(57) ABSTRACT

An extracorporeal blood treatment system including a gas exchange module operatively associated with a gas supply unit and optional pump for removing $CO_2$ from blood. The gas exchange module includes a plurality of short conduits that are uniquely configured and arranged in a gas exchange mat to for efficient $CO_2$ diffusion under conditions of low blood flow.

19 Claims, 8 Drawing Sheets

38
10
12
22a
22b
22d
14
16
22c
20

Related U.S. Application Data

(60) Provisional application No. 61/802,335, filed on Mar. 15, 2013.

(51) Int. Cl.
*A61M 1/36* (2006.01)
*A61M 1/16* (2006.01)

(52) U.S. Cl.
CPC ....... *B01D 19/0031* (2013.01); *B01D 63/026* (2013.01); *A61M 1/3609* (2014.02); *A61M 2205/3334* (2013.01); *A61M 2205/3368* (2013.01); *A61M 2230/202* (2013.01); *A61M 2230/205* (2013.01); *A61M 2230/208* (2013.01); *B01D 2313/90* (2013.01)

(56) References Cited

U.S. PATENT DOCUMENTS 4,698,207 A 10/1987 Bringham et al.
4,911,846 A 3/1990 Akasu et al.
4,948,560 A * 8/1990 Deguchi ............. A61M 1/1698 128/DIG. 3
5,270,005 A 12/1993 Raible
5,411,706 A 5/1995 Hubbard et al.
5,480,553 A 1/1996 Yamamori et al.
5,855,201 A * 1/1999 Fukui .................... B01D 53/22 128/200.11
5,865,789 A 2/1999 Hattler
6,620,319 B2 9/2003 Behmann et al.
7,641,853 B2 1/2010 Cattaneo et al.
7,927,544 B2 4/2011 Federspiel et al.
8,133,195 B2 3/2012 Blicke et al.
8,215,261 B2 7/2012 Helff et al.
9,095,817 B2 8/2015 Maurer
2002/0143397 A1 10/2002 von Segesser
2003/0039582 A1* 2/2003 Chambers ........... A61M 1/1698 422/44
2005/0077228 A1 4/2005 Pasqualini
2005/0232811 A1 10/2005 Autschbach et al.
2007/0020142 A1* 1/2007 Federspiel .......... A61M 1/1698 422/45
2007/0093749 A1 4/2007 Spranger
2007/0166190 A1* 7/2007 Ogihara ............. A61M 1/1698 422/45
2007/0249197 A1 10/2007 Spranger et al.
2007/0254856 A1 11/2007 Phillip et al.
2007/0276508 A1 11/2007 Fischer et al.
2007/0278145 A1* 12/2007 Taylor ................ B01D 19/0031 210/321.6
2008/0188806 A1 8/2008 Cattaneo et al.
2009/0017128 A1 1/2009 Monzyk et al.
2009/0035386 A1 2/2009 Matheis et al.
2009/0187133 A1 7/2009 Matheis et al.
2009/0254022 A1 10/2009 Cattaneo et al.
2010/0101657 A1 4/2010 Morley et al.
2011/0038760 A1 2/2011 Monzyk et al.
2011/0226686 A1 9/2011 Maurer
2011/0276036 A1 11/2011 Spranger et al.
2012/0190103 A1 7/2012 Maurer

FOREIGN PATENT DOCUMENTS

DE 102008024835 A1 12/2009
DE 10 2009 008 601 A1 8/2010
EP 0041692 B1 5/1984
EP 0 306 613 A1 3/1989
EP 0353148 A2 1/1990
EP 0 306 613 B1 12/1991
EP 0521495 A2 1/1993
EP 1433491 A2 6/2004
EP 1 522 323 A1 4/2005
EP 1524000 A2 4/2005
EP 1524000 A3 6/2005
EP 1524000 A8 10/2005
EP 1649882 A1 4/2006
EP 1649883 A1 4/2006
EP 1698362 A1 9/2006
EP 1762257 A1 3/2007
EP 1 810 704 A2 7/2007
EP 1847594 A2 10/2007
EP 1 864 709 A2 12/2007
EP 1525013 B1 12/2007
EP 1894593 A2 3/2008
EP 1595557 B1 4/2008
EP 1595558 B1 4/2008
EP 1595559 B1 4/2008
EP 1911475 A2 4/2008
EP 1595554 B1 5/2008
EP 1595555 B1 5/2008
EP 1595556 B1 5/2008
EP 2020247 A2 2/2009
EP 1847269 B1 6/2010
EP 1894593 B1 4/2011
EP 1845298 B1 1/2012
GB 1267105 A 3/1972
GB 1415946 A 12/1975
JP H02-086817 A 3/1990
JP 2000 084369 A 3/2000
JP 2007-215992 A 8/2007
JP 2012-517307 A 8/2012
WO 03061727 A2 7/2003
WO 2004016300 A2 2/2004
WO 2005/075007 A1 8/2005
WO 2008/135282 A2 11/2008
WO 2010025926 A1 3/2010
WO 2010091867 A1 8/2010

OTHER PUBLICATIONS

Search Report for EP Application No. 13168103.3, dated Oct. 27, 2014.
Search Report for CN Application No. 2014800241985, completed Nov. 28, 2016.
International Preliminary Report on Patentability for International Application No. PCT/IB2014/001600, dated Sep. 15, 2015.
Official Action and Search Report for JP Application No. 2015-562424, dated Feb. 27, 2018, which corresponds to the present application.
Ai_Ping et al., "In-Hosptial and 5-Year Mortality of Patients Treated in the ICU for Acute Exacerbation of COPD", Chest, 2005, vol. 128:2, pp. 518-524.
Bartlett et al., "Extracorporeal Membrane Oxygenation (ECMO) Cardiopulmonary Support in Infancy", Trans. Amer. Soc. Artif. Int. Organs, 1976, vol. 22, pp. 80-91.
Bensberg et al., "Artificial lung and exracorporeal gas exchange", Panminerva Med, 2005, vol. 47:1, pp. 11-17.
Bernard et al., "The American-European Consensus Conference on ARDS Definitions, Mechanisms, Relevant Outcomes, and Clinical Trial Coordination", Am J Respir Crit Care Med, 1994, vol. 149, pp. 818-824.
Broome et al., "Prolonged Extracorporeal Membrane Oxygenation and Circulatory Support as Bridge to Lung Transplant", Journal Athoracsur, 2008, Vpl. 86, pp. 1357-1360.
Brunston et al., "Total Arteriovenous CO2 Removal: Simplifying Extracorporeal Support for Respiratory Failure", The Society of Thoracic Surgeons, 1997, vol. 64, pp. 1599-1605.
Budweiser et al., "Health-Related quality of life and long-term prognosis in chronic hypercapnic respiratory failure: a prospective survival analysis", Respiratory Research, 2007, vol. 8:92, pp. 1-9.
Cochran et al., "Pediatric extracorporeal membrane oxygenation (ECMO): A Review of the First Ten Years of Experience at the Medical University of South Carolina", The Journal of the South Carolina Medical Association, 2005, vol. 101, pp. 104-107.
Combes et al., "Extracorporeal membrane oxygenation for respiratory failure in adults", www.co-criticalcare.com, 2012, vol. 18:1, pp. 99-104.
Combes et al., "Extracorporeal Membrane Oxygenation for 2009 Influenza A (H1N1)-Associated Acute Respiratory Distress Syndrome", Seminars in Respiratory and Critical Care Medicine, 2011, vol. 32:2, pp. 188-193.

(56) References Cited

OTHER PUBLICATIONS

Connors et al., "Outcomes Following Acute Exacerbation of Severe Chronic Obstructive Lung Disease", Am J. Respir Crit. Care Med, 1996, vol. 154, pp. 959-967.
Cordell-Smith e al., "Traumatic lung injury treated by extracorporeal membrance oxygenation (ECMO)", Injury, Int. J. Care Injured. 2006, vol. 37, pp. 29-32.
Dalal et al., "Clinical and Economic Burden of Depression/Anxiety in Chronic Obstructive Pulmonary Disease Patients with a Managed Care Population", COPD: Journal of Chronic Obstructive Pulmonary Disease, 2011, pp. 293-299.
Dalton et al., "Update on Extracorporeal Life Support 2004", Seminars in Perinatology, 2005. pp. 24-33.
Dalton, "Extracorporeal Life Support: Moving at the Speed of Light". Respiratory Care, 2011, vol. 56:9, pp. 1450-1456.
Davies, "Extracorporeal Membrane Oxygenation for 2009 Influenza A(H1N1) Acute Respiratory Distress Syndrome", JAMA, 2009, vol. 302:17, pp. 1888-1895.
Deslauriers et al., "Is Extracorporeal CO2 Removal an Option in the Treatment of Adult Respiratory Distress Syndrome?", Ann. Thorac. Surg., 1997, vol. 64, pp. 1581-1582.
Fischer et al., "Bridge to lung transplantation with the novel pumpless interventional lung assist device NovaLung", The Journal of Thoracic and Cardiovascular Surgery, 2006, vol. 131:3, pp. 719-723.
Formica et al., "Extracorporeal Membrane Oxygenation With a Poly-Methylpentene Oxygenator (Quadrox D). The Experience of a Single Italian Centre in Adult Patients With Refractory Cardiogenic Shock", ASAIO Journal, 2008, pp. 89-94.
Foster et al., "Assessment of the Economic Burden of COPD in the U.S.: A Review and Synthesis of the Literature", COPD: Journal of Chronic Obstructive Pulmonary Disease, 2006, pp. 212-218.
Gattiononi et al., "Clinical review: Extracorporeal membrane oxygenation", Critical Care, 2011, vol. 15:243, pp. 1-6.
Gramaticopolo et al., "Extracorporeal CO2 Removal—A Way to Achieve Ultraprotective Mechanical Ventilation and Lung Support: The Missing Piece of Multiple Organ Support Therapy", Cardiorenal Syndromes in Critical Care, 2010, vol. 165, pp. 174-184.
Grasselli et al., "Management of acute respiratory complications from influenza A (H1N1) infection: experience of a tertiary-level Intensive Care Unit", Minerva Anestesiologica, 2011, vol. 77:9, pp. 884-891.
Haneya et al., "Extracorporeal Circulatory Systems as a Bridge to Lung Transplantation at Remote Transplant Centers", Ann Thorac Surg, 2011, vol. 91, pp. 250-256.
Hill et al., "Prolonged Extracorporeal Oxygenation for Acute Post-Traumatic Respiratory Failure (Shock-Lung Syndrome)", New England Journal of Medicine, 1972, pp. 629-634.
Hines, "ECMO and Congential Heart Disease", Seminars in Perinatology, 2005, vol. 29, pp. 34-39.
Jones et al., "Long-term Results of ECMO for Adult Respiratory Failure", pp. 417-430, No date.
Michael, "Fundamentals of Medical Physiology", 2011, Thieme Medical Publishers, Inc., p. 50.
Moen et al., "Differences in blood activation related to roller/centrifugal pumps and heparin-coated/uncoated surfaces in a cardiopulmonary bypass model circuit", Perfusion, 1996, vol. 11, pp. 113-123.
Mosucci, "Complications of Cardiovascular Procedures", 2010, p. 409.
Nishinaka et al., "Up to 151 days of continuous animal perfusion with trivial heparin infusion by the application of a long-term durable antithrombogenic coating to a combination of a seal-less centrifugal pump and a diffusion membrane oxygenator", J. Artif Organs, 2007, vol. 10, pp. 240-244.
Oda et al., "Trends in and perspectives on extracorporeal membrane oxygenation for severe adult respiratory failure", Gen Thorac Cardiovasc Surg., 2017, vol. 60:4, pp. 192-201 (Abstract Only).
Peek et al., "ECLS for Adult Respiratory Failure: Etiology and Indications", Sug, 2003; vol. 76, pp. 390-402.
Peek et al., "Efficacy and economic assessment of conventional ventilatory support versus extracorporeal membrane oxygenation for severe adult respiratory failure (CESAR): a multicentre randomised controlled trial", Lancet, 2009, vol. 374, pp. 1351-1363.
Pesenti et al.,"Extracorporeal gas exchange", Current Opinion in Critical Care, 2009, vol. 15, pp. 52-58.
Pesenti et al., "Carbon dioxide dialysis will save the lung", Crit Care Med, 2010, vol. 38:10, pp. S549-S554.
Plant et al., "Early use of non-invasive ventilation for acute exacerbations of chronic obstructive pulmonary disease on general respiratory wards: a multicentre randomised controlled trial", The Lancet, 2000, vol. 355:9219, pp. 1931-1935 (Abstract Only).
Polkey et al., "Attacking the disease spiral in chronic obstructive pulmonary disease: an update", Clinical Medicine 2011, vol. 11:5, pp. 461-464.
Ruberto et al., "Extracorporeal Removal CO2 Using a Venovenous, Low-Flow System (Decapsmart) in a Lung Transplanted Patient: A Case Report", Transplantation Proceedings, 2009, vol. 41, pp. 1412-1414.
Strassels et al., "The Costs of Treating COPD in the United States", Chest, 2001, vol. 119:2, pp. 344-352.
Sullivan et al., "The Economic Burden of COPD", Chest, 2000, vol. 117:2, pp. 5S-9S.
Terragni et al.,"Role and potentials of low-flow CO2 removal system in mechanical ventilation", www.co-criticalcare.com, 2012, vol. 18:1, pp. 93-98.
Terragni et al. "Extracorporeal CO2 Removal", Cardiorenal Syndromes in Critical Care, 2010, Karger, New York.
Terragni et al., "Tidal Volume Lower than 6 ml/kg Enhances Lung Protection", Anesthesiology, 2009, vol. 111, pp. 826-835.
Tsolaki et aL, "One-year non-invasive ventilation in chronic hypercapnic COPD: Effect on quality of life", Respiratory Medicine, 2008, vol. 102, pp. 904-911.
Weber-Carstens et al., "Hypercapnia in late-phase ALI/ARDS: providing spontaneous breathing using pumpless extracorporeal lung assist", Intensive Care Med, 2009, vol. 35, pp. 1100-1105.
Yamagishi et al., "Clinical Results of Extracorporeal Membrane Oxygentation (ECMO) Support for Acute Respiratory Faiure: A Comparison of a Centrifugal Pump ECMO with a Roller Pump ECMO", Surg Today, 2004, vol. 34, pp. 209-213.
Zwischenberger et al., "Intravascular Membrane Oxygenation and Carbon Dioxide Removal with IVOX: Can Improved Design and Permissive Hypercapnia Achieve Adequate Respiratory Support During Severe Respiratory Failure", Artificial Organs, 1994, vol. 8:11, pp. 833-839.
Pesenti et al., Low Frequency Positive Pressure Ventilation With Extracorporeal CO2 Removal (LEPPV-ECCO2R) In Acute Respiratory Failure (ARF): Technique, Trans Am Soc Artif Intern Organs, 1981, 263-266, vol. XXVII.
Baker et al., Extracorporeal carbon dioxide removal (ECCO2R) in respiratory failure: an overview, and where next?, JICS, Jul. 2012, 232-237, vol. 13, No. 3.
Rambaud et al., A pilot study comparing two polymethylpentene extracorporeal membrance oxygenators, Perfusion, Jan. 14-20, 2013, vol. 28, No. 1 (Abstract).
Maquet Getinge Group, Pump Assisted Lung Protection Cardiohelp System, May 2010, 8 pages.
Lubnow, Extracorporeal CO2 Elimination Clinical Application, ESICM 2011 Berlin, 31 pages.
Novalung GmbH, Novalung Solutions for Lung Failure, iLA active, The all-rounder for extrapulmonary lung support, No date.
Maquet Getinge Group, Low Flow CO2 Removal: Palp Pump Assisted Lung Protection, Sep. 2011, 10 pages.
Maquet Getinge Group, Meeting the Needs of the Smallest Patients Quadrox-i Neonatal and Pediatric, Sep. 2009, 6 pages.
Babu, Ecmo: The best therapy for severe ARDS, Alan Hopeman Lectureship, Sep. 27, 2010, 43 pages.
Weber-Carstens, Is hypercapnia with respiratory acidosis in acute lung failure acceptable or detrimental?, ESICM 2011: PALP—Complementation of Respiratory Therapy, 31 pages.
Pesenti, Extracorporeal CO2 Removal Indications and limitations, Powerpoint presentation, University of Milano Bicocca, Ospedale San Gerardo Monza, Italy, 8 pages. No date.

(56) References Cited

OTHER PUBLICATIONS

Moher et al, Das CONSORT Statement: Überarbeitete Empfehlungen zur Qualitätsverbesserung von Reports randomisierter Studien im Parallel-Design, Dtsch Med Wochenschr, 2004, T16-T20, vol. 129.
Office Action for counterpart CN Application No. 201480024198.5, dated Dec. 6, 2016.
Office Action for counterpart EP Application No. 13168103.3, dated Sep. 20, 2017.
Office Action for counterpart CN Application No. 201480024198.5, dated Aug. 21, 2017.
EPO Invitation to Attend Oral Proceedings issued on Sep. 28, 2018 for corresponding EP Patent Application No. 13168103.3, 7 pages (English Translation also attached, 7 pages).
Final Official Action issued in counterpart JP Application No. 2015562424, dated Oct. 22, 2018.

* cited by examiner

CARBON DIOXIDE REMOVAL SYSTEM

This application is a continuation-in-part application pursuant to 35 U.S.C. 365(c) of International Application No. PCT/IB2014/001600, filed Mar. 14, 2014, which claims benefit of priority to U.S. Provisional Patent Application No. 61/802,335, filed Mar. 15, 2013, and European Patent Application No. 13168103.3, filed May 16, 2013. The disclosures of these applications are herein incorporated by reference in their entirety.

BACKGROUND OF THE INVENTION

Field of the Invention

The present invention is directed to a carbon dioxide removal system and methods for use thereof. In particular, the invention may be useful for treating diseases, syndromes, injuries, defects or other conditions affecting lung function, including chronic obstructive pulmonary disease (COPD), chronic and acute hypercapnia, respiratory acidosis, acute lung injury (ALI), and acute respiratory distress syndrome (ARDS).

Description of the Related Technology

The primary functions of the lung are oxygenation and elimination of carbon dioxide ($CO_2$) from blood. Currently, treatments for respiratory problems are primarily focused on addressing and enhancing oxygenation. Ventilation, for example, is the standard of care for COPD, which inhibits expiration of $CO_2$, and persistently elevated levels of $CO_2$ caused by hypercapnia. Mechanical ventilation, however, is an invasive therapy, the associated applied pressures of which induce shear stress, over distention, cyclic stretching, lesions of the alveolar-capillary membrane and other forms of tissue damage. These physiological injuries along with the increased intrathoracic pressure associated with mechanical ventilation further impair alveolar-capillary permeability, decrease cardiac output and impede organ perfusion. Furthermore, mechanical ventilation increases the risk of complications, such as ventilator associated pneumonia (VAP), can require sedation of the patient.

Alternative protective ventilation therapies, such as extracorporeal membrane oxygenation (ECMO), has fewer negative side-effects than mechanical ventilation. High blood flow is necessary to drive the low tidal oxygenation and of ECMO therapy. This large blood flow, however, increases patient risk in the event of blood leakage and requires the use of large, invasive cannulas and needles causing patient trauma. Furthermore, ECMO has thus far only been proven safe and effective for treating select respiratory diseases.

Another type of protective ventilation therapy is provided by a combination oxygenator and $CO_2$ removal device. This device is designed for low blood flow resistance and therefore does not require a pump for arterial venous use. Additionally, the device utilizes long gas exchange fibers that are adapted for large mass transfer of gas, which is in efficient for $CO_2$ removal.

In light of the above, there exists is a need to develop an improved respiratory treatment system and therapy that is safe, relatively non-invasive and that effectively removes $CO_2$ from the blood.

SUMMARY OF THE INVENTION

An extracorporeal blood treatment system according to an example embodiment of the present invention comprises a gas exchange module configured to provide a passageway for blood and to remove carbon dioxide from the blood as the blood passes through the gas exchange module. The gas exchange module comprises a plurality of conduits, wherein each conduit comprises an exterior surface and an interior luminal surface and wherein the interior luminal surface defines a passageway. At least some of the conduits comprise pores, wherein upon exposure of the blood to the exterior surface all of the conduits comprising pores have a first length that allows for diffusion of carbon dioxide from the blood to the passageway.

An extracorporeal blood treatment system according to an example embodiment of the present invention comprises a gas exchange module configured to provide a passageway for blood and to remove carbon dioxide from the blood as the blood passes through the gas exchange module. The gas exchange module comprises a plurality of conduits at least partially contained in the gas exchange module, wherein each conduit comprises an interior luminal surface defining a passageway and an exterior surface. At least some of the conduits comprise pores, and all of the conduits that comprise pores have a first length along the conduits allowing for the diffusion of carbon dioxide from the blood contained outside the conduits but inside the gas exchange module, to the passageway upon exposure of the blood to the exterior surface of the conduits. The first length of at least one of the conduits that comprise pores is about 5.8 cm or less.

An extracorporeal blood treatment system according to an example embodiment of the present invention comprises a gas exchange module configured to provide a passageway for blood and to remove carbon dioxide from the blood as it passes through the gas exchange module. The gas exchange module comprises a plurality of conduits at least partially contained in the gas exchange module, wherein at least one conduit is configured to provide a passageway for gas and to allow for diffusion of carbon dioxide from the blood through a wall of the at least one conduit and to the passageway upon exposure of the blood to an exterior surface of the at least one conduit and wherein the at least one conduit has a first length available for carbon dioxide diffusion of about 5.8 centimeters or less. The extracorporeal blood treatment system does not have a heat exchanger adapted for regulating the temperature of the blood.

An extracorporeal blood treatment system according to an example embodiment of the present invention comprises a gas exchange module configured to provide a passageway for blood and remove carbon dioxide from the blood as the blood passes through the gas exchange module. The gas exchange module comprises a plurality of conduits at least partially contained in the gas exchange module, wherein at least one conduit is configured to provide a passageway for gas and to allow for diffusion of carbon dioxide from the blood contained outside the conduits but inside the gas exchange module to the passageway upon exposure of the blood to an exterior surface of the at least one conduit and wherein the at least one conduit has a surface area available for carbon dioxide diffusion of about 5.42×10-5 $m^2$ to about 7.85×10-5 $m^2$. The extracorporeal blood treatment system does not have a heat exchange mechanism.

An extracorporeal blood treatment system according to an example embodiment of the present invention comprises a gas exchange module configured to provide a passageway for blood and remove carbon dioxide from the blood as it passes through the gas exchange module. The gas exchange module comprises a plurality of conduits at least partially contained in the gas exchange module and arranged to form a gas exchange mat, wherein at least one conduit is configured to provide a passageway for gas and to allow for diffusion of carbon dioxide from the blood upon exposure of the blood to an exterior surface of the at least one conduit and wherein a ratio of a first length of the at least one conduit to a total thickness of the gas exchange mat is about 1:1 or less. The extracorporeal blood treatment system does not have a heat transfer mechanism.

An extracorporeal blood treatment system according to an example embodiment of the present invention comprises a gas exchange module configured to provide a passageway for blood and remove carbon dioxide from the blood as it passes through the gas exchange module. The gas exchange module includes a plurality of conduits forming one or more gas exchange mats, wherein at least one conduit is configured to provide a passageway for gas and to allow along a first length of the at least one conduit diffusion of carbon dioxide from the blood upon exposure of the blood to an exterior surface of the at least one conduit. A ratio of the first length to a total thickness of the gas exchange mats is about 3:1 or less, about 2:1 or less and about 1:1 or less.

According to an example embodiment, a collective average of the first lengths of the conduits that comprise pores is about 5.8 cm or less.

According to an example embodiment, at least one of the plurality of conduits has an outer diameter of about 350 μm to about 410 μm.

According to an example embodiment, all of the conduits that comprise pores have an average outer diameter of about 350 μm to about 410 μm.

According to an example embodiment, a first length of at least one of the conduits that comprise pores is about 76.3% or less than a full length of the at least one of the conduits that comprise pores.

According to an example embodiment, an average of the first length of all of the conduits that comprise pores is about 76.3% or less than an average of the full length of all of the conduits that comprise pores.

According to an example embodiment, an exposed surface area of the at least one conduit is about 5.71×10-5 $m^2$ to about 7.47×10-5 $m^2$.

According to an example embodiment, the pores of the conduits that comprise pores are about 0.2 microns or less.

According to an example embodiment, the at least one conduit is constructed from polymetheylpentene.

According to an example embodiment, all of the conduits that comprise pores are constructed from polymetheylpentene.

According to an example embodiment, the at least one conduit has a microporous microstructure covered by a thick and impervious diffusion layer membrane.

According to an example embodiment, the conduits that comprise pores are arranged in a crisscrossing pattern.

According to an example embodiment, the conduits that comprise pores are arranged to form conduit layers located between a blood inlet and a blood outlet of the gas exchange module, the blood inlet faces the conduit layers such that the blood flows towards the conduit layers in a direction substantially orthogonal to the conduit layers.

According to an example embodiment, each conduit layer is comprised of two or more of the conduits that comprise pores arranged substantially parallel to one another.

According to an example embodiment, the two or more of the conduits that comprise pores and are arranged substantially parallel to one another are knitted or woven together by a separate thread or thread-like structure.

According to an example embodiment, the conduits of adjacent conduit layers are oriented substantially perpendicular to one another.

According to an example embodiment, the gas exchange module comprises at least about 10,000 conduits that comprise pores, at least about 12,000 conduits that comprise pores, at least about 13,000 conduits that comprise pores, or at least about 13,119 conduits that comprise pores.

According to an example embodiment, a combined surface area available for carbon dioxide diffusion of all conduits that comprise pores is about 0.98 $m^2$ or more.

According to an example embodiment, a combined surface area available for carbon dioxide diffusion of all conduits that comprise pores is about 0.92 $m^2$ or more, about 0.95 $m^2$ or more, about 0.98 $m^2$ or more.

According to an example embodiment, the system further comprises a pump operatively associated with the gas exchange module for directing and regulating a flow of the blood to the gas exchange module, wherein the pump is adapted to deliver the blood to the gas exchange module at rate of about 1 L/min or less.

According to an example embodiment, the system further comprises a pump operatively associated with the gas exchange module for directing and regulating a flow of the blood to the gas exchange module, wherein the pump is adapted to deliver the blood to the gas exchange module at rate between about 0.2 L/min to about 0.8 L/min.

According to an example embodiment, the gas exchange module comprises a pressure sensor positioned adjacent to the blood outlet and in direct contact with the blood exposed to the conduits that comprise pores for measuring blood pressure as the blood exits the gas exchange module.

According to an example embodiment, the gas exchange module further comprises a gas inlet and gas outlet, wherein all of the conduits of the gas exchange module that comprise pores are in fluid communication with the gas inlet.

According to an example embodiment, the system does not include a heat exchange mechanism.

According to an example embodiment, the system does not regulate the temperature of any fluid entering or leaving the gas exchange module.

According to an example embodiment, the system further comprises a cannula operatively associated with the gas exchange module, wherein the cannula has a size of about 21 French (7 mm) or less, about 19 French (6.33 mm) or less, about 16 French (5.33 mm) or less, or about 13 French (4.33 mm) or less.

According to an example embodiment, the cannula is a double-lumen cannula.

According to an example embodiment, a combined volume of the conduits of the gas exchange module that comprise pores is about 0.085 liters to about 0.100 liters.

According to an example embodiment, the plurality of conduits form one or more gas exchange mats, and the ratio of the first length of the at least one conduit to a total thickness of the gas exchange mat is about 3.0 or less.

According to an example embodiment, the system is configured for carbon dioxide removal from the blood with at most only nominal diffusion of oxygen to the blood.

A method for removing carbon dioxide from blood according to an example embodiment of the present invention uses a blood treatment system comprising a gas exchange module configured to provide a passageway for blood and remove carbon dioxide from the blood as it passes through the gas exchange module. The gas exchange module comprises a plurality of conduits at least partially contained in the gas exchange module, wherein at least one conduit is configured to provide a passageway for gas and to allow for diffusion of carbon dioxide from the blood to pass to the passageway upon exposure of the blood to an exterior surface of the at least one conduit and wherein at least one conduit has a first length available for carbon dioxide diffusion of about 5.8 cm or less. The method for using the blood treatment system comprises: selecting a gas exchange module to treat a human including an adult human; flowing the blood into the gas exchange module at a rate of 1 liter per minute or less; and exposing the blood to a plurality of conduits that comprise pores to remove carbon dioxide from the blood.

According to an example embodiment, the method involves flowing blood into the gas exchange module at a rate of about 0.51 liters per minute or less or between about 0.4 liters per minute to about 0.51 liters per minute.

According to an example embodiment, the method involves flowing gas through the conduits at a rate of 0.2 liters per minute to 15 liters per minute.

According to an example embodiment, the method involves flowing gas through the conduits at a rate of more than about 15 liters per minute.

According to an example embodiment, the method involves selecting a gas that has a partial pressure of carbon dioxide that is zero or at least lower than a partial pressure of carbon dioxide of the blood flowing into the gas exchange module.

According to an example embodiment, the method involves treating the blood without regulating blood temperature.

According to an example embodiment, wherein throughout the length of the at least one conduit, there exists a carbon dioxide gradient between a gas flowing through the at least one conduit and the blood exposed to the exterior surface of the at least one conduit.

According to an example embodiment, wherein the carbon dioxide gradient is substantially constant along the length of the at least one conduit.

According to an example embodiment, the method involves after said step of exposing, measuring blood pressure using a sensor of the gas exchange module in direct contact with the blood exposed to the conduits after exposing the blood to the plurality of conduits.

According to an example embodiment, the method involves measuring the amount of carbon dioxide removed from the blood using a sensor of the gas exchange module.

According to an example embodiment, the conduits are arranged in layers and are located between a blood inlet and a blood outlet of the gas exchange module, and wherein the blood flows towards the conduits in a direction substantially orthogonal to the length of the conduits.

According to an example embodiment, the method involves obtaining from a venous blood source the blood delivered to the gas exchange module and treating the blood such that a partial pressure of carbon dioxide in the blood after exposure to the conduits is about 50 mm Hg to about 70 mm Hg.

According to an example embodiment, the method involves obtaining from a venous blood source the blood delivered to the gas exchange module and treating the blood such that a pH value of the blood exposed to the conduits is about 7.25 to about 7.35.

According to an example embodiment, the method involves extracting from a venous circulatory system the blood delivered to the gas exchange module and returning the blood treated by the gas exchange module to the venous circulatory system.

According to an example embodiment, the blood is treated by the gas exchange module for a period of about 6 hours to about 30 days.

According to an example embodiment, the method involves using the blood treatment system to remediate a respiratory condition in the adult human selected from the group consisting of chronic obstructive pulmonary disease, acute lung injury, acute respiratory distress syndrome and hypercapnia.

According to an example embodiment, the method involves treating the blood by removing carbon dioxide from the blood with no or at most only nominal diffusion of oxygen.

According to an example embodiment, the method for removing carbon dioxide is performed using any of the above described example blood treatment system embodiments.

An extracorporeal blood treatment system according to an example embodiment of the present invention comprises a gas exchange module configured to provide a passageway for blood and remove carbon dioxide from the blood as it passes through the gas exchange module. The gas exchange module comprises a plurality of conduits at least partially contained in the gas exchange module, wherein at least one conduit is configured to provide a passageway for gas and to allow for diffusion of carbon dioxide from the blood upon exposure of the blood to an exterior surface of the at least one conduit and wherein the at least one conduit has a length available for carbon dioxide diffusion of about 5.8 centimeters or less. The blood treatment system further includes a gas inlet and gas outlet, wherein all of the conduits of the gas exchange module are operatively associated with the gas inlet to permit fluid communication of the gas though the gas exchange module.

BRIEF DESCRIPTION OF THE DRAWINGS

FIG. 3(*b*) is a perspective view showing the internal housing components of the gas exchange module of FIG. 3(*a*), including a single blood treatment chamber without the gas exchange conduits.

FIG. 3(*c*) is a perspective view of another embodiment of the gas exchange module of FIG. 3(*b*) showing a frame dividing the blood treatment chamber into two compartments, each adapted for receiving a gas exchange mat.

FIG. 3(*d*) is a front view of the gas exchange module of FIG. 3(*a*).

FIG. 3(*e*) is a cross-sectional view of the gas exchange module of FIG. 3(*d*) taken at line A-A, showing a single, empty blood treatment chamber.

FIG. 3(*f*) is a cross-sectional view of the gas exchange module of FIG. 3(*d*) taken at line A-A, showing a blood treatment chamber with a gas exchange mat situated within the blood treatment chamber and illustrating the flow of gas through the gas exchange module.

FIG. 3(*g*) is a cross-sectional view of another embodiment of the gas exchange module of FIG. 3(*e*) corresponding to the embodiment of FIG. 3(*c*), showing a frame dividing the blood treatment chamber into two compartments that fluidly communicate with one another as best shown in FIG. 3(*c*), each compartment containing a gas exchange mat.

FIG. 3(*h*) is an overhead view of the blood treatment system of FIG. 3(*a*).

FIG. 3(*i*) is a cross-sectional view of the gas exchange module of FIG. 3(*h*) at line B-B illustrating the flow of gas through the gas exchange module.

FIG. 3(*j*) is a cross-sectional view of the gas exchange module of FIG. 3(*i*) at line D-D.

FIG. 3(*k*) is a two dimensional schematic diagram of two adjoining conduit layers of the gas exchange mat showing the perpendicular orientation of the conduit layers.

FIG. 3(*l*) is a three dimensional diagram of a portion of a conduit layer showing a plurality of parallel conduits.

FIG. 3(*m*) is a two dimensional schematic diagram of two adjoining conduit layers of the gas exchange mat showing the relative perpendicular orientation of the conduit layers.

FIG. 3(*n*) is a cross-sectional view of the gas exchange module of FIG. 3(*h*) at line C-C.

DETAILED DESCRIPTION OF THE PREFERRED EMBODIMENTS

Figure 1:
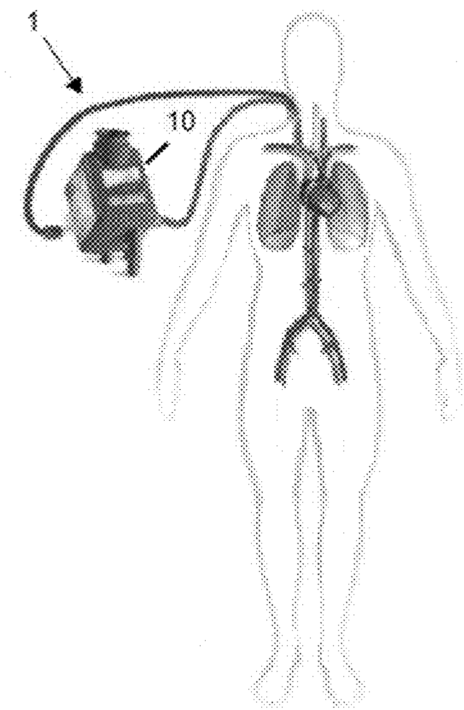
FIG. 1 is a diagram showing an exemplary blood treatment system attached to a patient's jugular vein using a dual lumen catheter and including a gas exchange module.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Thus, for example, reference to "a conduit" may include a plurality of conduits and equivalents thereof known to those skilled in the art, and so forth. As well, the terms "a" (or "an"), "one or more" and "at least one" can be used interchangeably herein. It is also to be noted that the terms "comprising," "including," "composed of," and "having" can be used interchangeably.

For purposes of the present invention, the "active length" or "active portion" of a conduit refers to the collective lengths or portions of a conduit having a surface area that allows for passage of gas through the conduit, particularly $CO_2$ diffusion. For example, the active length or active portion may be the total lengths or portions of a conduit membrane having pores that are at least substantially unimpeded and allow for gas exchange through the conduit via the pores.

As used herein the "inactive length" or "inactive portion" of a conduit refers to the collective lengths or portions of the conduit incapable of passage of gas through the conduit, particularly incapable of $CO_2$ diffusion. For example, the inactive length or inactive portion may be the total lengths or portions of a conduit potted within a matrix such that any pores of the potted length or portion are blocked or otherwise prevented from the transfer of gas through the conduit wall.

As used herein, "non-physiological values" of the partial pressure of $CO_2$ in blood or of blood pH refers to values of $CO_2$ partial pressure or blood pH that are not within the standard accepted physiological range. For example, for blood taken from the arterial system, normal physiological values of $pCO_2$ of the blood typically may be about 32-46 mm Hg and normal value of pH may be about 7.45; for blood taken from the venous system, normal physiological values of $pCO_2$ of the blood typically may be about 38-54 mm Hg and normal values of pH may be about 7.35.

As used herein, "property of blood" refers to a physiological characteristic or component of blood. Exemplary properties include temperature, composition and partial pressure or $CO_2$ content.

Furthermore, "treating" as used herein refers to improving, alleviating or remedying a disease, syndrome, injury and defect, other condition, or an associated symptom thereof.

The present invention is directed to a novel extracorporeal blood treatment system and therapeutic method for efficiently, effectively and safely removing $CO_2$ from a patient's blood stream in a minimally invasive manner. In an exemplary embodiment, the invention is adapted to directly access a patient's vascular system, the extracorporeal blood treatment system is specifically designed to remove substantially all the $CO_2$ from a flow of a patient's blood passing through a gas exchange module of the system at a low flow rate in a single pass. The invention may be used for various applications, including treating respiratory conditions, such as COPD, chronic and acute hypercapnia, respiratory acidosis, acute lung injury, acute respiratory distress syndrome and hypercapnia, by substantially eliminating $CO_2$ from blood circulating in a patient.

Blood Treatment System

Figure 2:
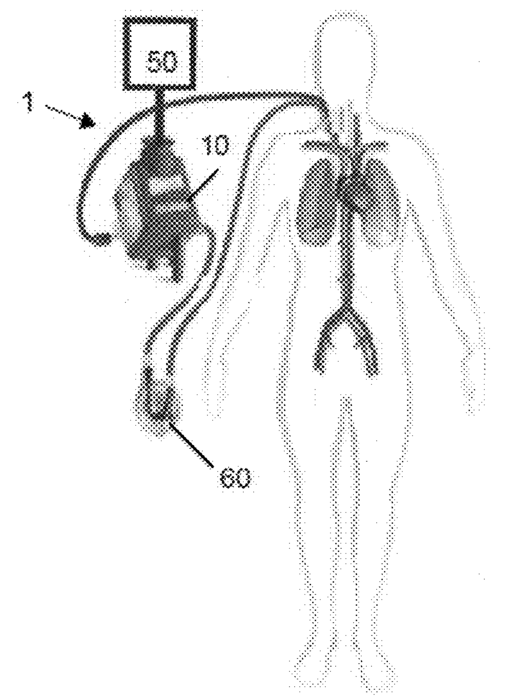
FIG. 2 is a diagram showing an exemplary blood treatment system attached to a patient's jugular vein using a dual lumen catheter and including a gas exchange module operatively associated with a gas supply unit and a pump.

FIGS. 1-2 illustrate exemplary embodiments of the extracorporeal blood treatment system 1 of the present invention, which include a gas exchange module 10 having a plurality of conduits 30, at least some or all of which are configured to alter a property of blood flowing through gas exchange module 10. In particular, gas exchange module 10 includes a plurality of short conduits 30 each having a gas permeable membrane, wherein conduits 30 are uniquely configured and arranged in one or more gas exchange mats 34 for efficient gas diffusion, such as efficient $CO_2$ diffusion. In an exemplary embodiment, gas exchange module 10 is configured as a gas transfer device having a plurality of gas permeable conduits 30 specifically designed and adapted for $CO_2$ diffusion. Blood treatment system 1 may optionally further include a gas supply unit 50 that delivers a stream of gas through the lumens of conduits 30 while blood passes through gas exchange module 10 contacting and flowing past an exterior surface of conduits 30 at a low flow rate. Gas diffusion, specifically $CO_2$ diffusion, from the blood and through the gas permeable membrane of conduits 30 is driven by the difference in gas partial pressure, e.g. $CO_2$ partial pressure, between the gas flowing through conduits 30 and the gas partial pressure, e.g. $CO_2$ partial pressure, of the patient's blood exposed to and flowing around conduits 30. Gas supply unit 50 supplies gas at a high velocity gas flow rate through conduits 30 to maximize and maintain the driving force of gas diffusion, e.g. $CO_2$ diffusion, along the length active length of conduit 30. Blood treatment system 1 may optionally further include a pump 60 and an integral or otherwise operatively associated control unit 62 for regulating the flow of blood through gas exchange module 10. In an exemplary embodiment, extracorporeal blood treatment system 1 is not designed to oxygenate the patient's blood and/or does not include a heat exchanger for heating or cooling blood delivered to, flowing through or exiting from the gas exchange module 10 or otherwise seek to change or regulate blood temperature.

FIGS. 3(*a*)-3(*m*) show an exemplary gas exchange module 10 having a housing 12 defining an internal cavity 13 through which blood is flowed and for at least partially containing a plurality of conduits 30 adapted for gas diffusion, in particular $CO_2$ diffusion. As shown in FIGS. 3(*a*)-3(*b*) and 3(*d*)-3(*f*), gas exchange module 10 includes a blood inlet port 14 and blood outlet port 16 spaced apart from one another and located on opposing faces of housing 12. A plurality of gas exchange conduits 30 are arranged between blood inlet and outlet ports 14, 16 such that blood entering blood inlet port 14 flows towards conduits 30 in a direction substantially orthogonal to the length of one or more, or all of conduits 30. The opening and length of elongated blood inlet and/or outlet ports 14, 16 may also be oriented substantially orthogonal to the length of one or more conduits 30. Gas exchange module 10 further includes a gas inlet port 18 and gas outlet port 20 for delivering gas to and from the plurality of conduits 30. Gas inlet and outlet ports 18, 20 are spaced apart from one another and may be aligned in the same plane as conduits 30 and oriented substantially orthogonal to blood inlet and outlet ports 14, 16 such that gas flowing through gas exchange module 10 is substantially orthogonal to blood flow through gas exchange module 10.

Conduits 30 may be configured as hollow, thin fibers or other tubules with a central lumen for gas passage, best shown in FIGS. 3(*k*)-3(*m*). These lumens provide a passageway through which gas is transported to induce $CO_2$ diffusion from blood contacting an exterior surface of conduit 30, through the conduit walls and into the conduit lumens. Conduits 30 may be configured to have a gas permeable membrane, such as a porous membrane including a plurality of pores adapted for gas diffusion, particularly $CO_2$ diffusion. In one embodiment, conduits 30 may have a microporous membrane, such as the microporous polypropylene hollow fiber manufactured by Polypore and marketed under the trade name OXYPAHAN having a maximum 2 micron pore size, or alternatively a diffusive membrane, such as the diffusive polymethylpentene hollow fiber membrane having a 55% porosity manufactured by Polypore and marketed under the trade name OXYPLUS. Conduits 30 may have the same or different degree of porosity and/or pore size. In one embodiment, the gas permeable membrane of conduit 30 may have a pore size or diameter of about 0.2 microns or smaller, which may be construed as a maximum pore size of about 0.2 microns. In one embodiment, the gas permeable membrane of conduits 30 may be configured to only permit gas passage, specifically $CO_2$ diffusion, inhibiting diffusion of liquids or solids. The gas permeable membrane may also be configured to inhibit blood plasma leakage. In one embodiment, conduits 30 may be configured to allow for $CO_2$ diffusion while preventing blood plasma leakage for up to at least 30 days under normal operating pressures and flow rates. Conduits 30 may be constructed from any gas permeable material that optionally also inhibits blood plasma leakage. In an exemplary embodiment, polymetheylpentene may be used to construct conduits 30.

While gas exchange module 10 may include other types of conduits different than gas exchange conduits 30, such as conduits which do not affect a property of blood, non-porous conduits which affect the property of blood, gas impermeable conduits which affect the property of blood, and/or porous conduits which allow for diffusion of gases other than $CO_2$, in one embodiment all the conduits of gas exchange module 10, inclusive of all the gas exchange conduits 30, are adapted for gas diffusion, such as $CO_2$ diffusion. In another embodiment, all the conduits of gas exchange module 10 that are configured to alter a property of blood, inclusive of gas exchange conduits 30, may be gas permeable and/or have a microporous membrane with pores adapted for gas diffusion, such as $CO_2$ diffusion.

Efficient removal of $CO_2$ using gas exchange module 10 under low blood flow rate conditions is achieved by the uniquely configured conduits 30 and/or the arrangement of a plurality of these conduits 30 to form one or more gas exchange mats 34 having a sufficient collective thickness to effectively diffuse $CO_2$ from blood. In an exemplary embodiment, gas exchange conduits 30 may have a short length that allows for decreased fluidic resistance of the gas, such as a high velocity stream of gas, flowing through the lumen, and therefore minimizes any pressure drop within and across conduit 30. Consequently, the low back pressure conditions within conduit 30 inhibits formation of potentially dangerous microbubbles on the exterior blood contacting surface of conduit 30 thereby preventing formation of an emboli in the blood. In one embodiment, conduit 30 may have a sufficiently short length that substantially prevents formation of microbubbles on an exterior of conduit 30 and/or a drop in gas flow pressures within and along the length of conduit 30 as gas is flowed through the conduit lumen at a predetermined, constant gas flow rate. In an exemplary embodiment, conduits 30 have a full length, illustrated as dimension X in FIGS. 3(*i*) and 3(*j*), of about 71 cm to about 81, about 71 cm to about 76 cm, or about 76 cm to about 81 cm.

Each conduit 30 has an elongated body including a proximal end 36 and distal end 38. As will be described in further detail below, when conduits 30, are positioned within, potted in, affixed to, attached to or otherwise disposed within a blood treatment chamber 24 located in the internal cavity 13 of housing 12, portions of conduit 30, particularly proximal and distal ends 36, 38, may be rendered incapable of gas transfer by virtue of the manner in which conduit 30 is attached to blood treatment chamber walls 26. This inactive portion or inactive length of a conduit 30, shown in FIG. 3(*i*) by the collective dimensions W of the total length X of one conduit 30, have pores that may be blocked and otherwise prevented from allowing localized gas diffusion, specifically $CO_2$ diffusion. In the illustrated embodiment, the inactive length of a conduit 30 is the sum of the two W dimensions of a total length X of one conduit 30. The remaining active portion or active length of conduit 30, shown in FIG. 3(*i*) as dimension Y, may allow for gas diffusion, in particular $CO_2$ diffusion. In the illustrated embodiment, one Y reference denotes the active length of the conduits 30 of a first conduit layer 32*a* (labeled as 32), and the other Y reference denotes the active length of the conduits 30 of an adjoining perpendicularly oriented second conduit layer 32*b* (not labeled) beneath conduit layer 32*a*. In an exemplary embodiment, the active length of the conduit 30 available for $CO_2$ diffusion may be about 5 cm to about 6 cm, about 5.2 cm to about 5.8 cm, about 5.2 cm to about 5.5 cm, or about 5.5 cm to about 5.8 cm. The percent of the active length of conduit 30 to the overall length of conduit 30 may be about 76.3% or less, about 40% to about 76.3%, about 68.4% to about 76.3%, or about 68.4% to about 72.4%. In another embodiment, the ratio of conduit active length to the total length of conduit 30 is about 0.724:1±5%, about 0.79:1 or less, about 0.77:1 or less. The ratio of conduit active length to conduit inactive length may be about 2.12:1 to about 3.22:1, about 2.12:1 to about 2.62:1, or about 2.62:1 to about 3.22:1. The available active surface area for $CO_2$ diffusion of a single conduit 30 may be $5.42\times10^{-5}$ m$^2$, about $5.42\times10^{-5}$ m$^2$ to about $7.85\times10^{-5}$ m$^2$, about $5.60\times10^{-5}$ m$^2$ to about $7.85\times10^{-5}$ m$^2$, about $5.71\times10^{-5}$ m$^2$ to about $7.47\times10^{-5}$ m$^2$, or about $5.71\times10^{-5}$ m$^2$ to about $7.01\times10^{-5}$ m$^2$. In an exemplary embodiment, the active surface area of a single conduit 30 may be about $5.71\times10^{-5}$ m$^2$±5% to about $7.47\times10^{-5}$ m$^2$±5%. The outer diameter of conduit 30 may be about 350 um to about 410 um. Additionally, the volume of conduit 30 may be about 0.085 L to about 0.100 L.

As best shown in FIGS. 3(*k*)-3(*m*), conduits 30 are arranged in a set and positioned substantially parallel to one another, wherein conduits 30 are bound to, attached to or otherwise connected to one another in order to form a thin conduit layer 32. Conduit layer 32 may be constructed from conduits 30 of the same or different configuration and/or dimensions, such as length and diameter. Conduits 30 and conduit layer 32 form a plurality of passages for gas to pass from one side of the gas exchange module 10 to an opposite side of gas exchange module 10. Additionally, conduit layer 32 is configured to allow for blood to pass between and around adjacent conduits 30. In one embodiment, the conduits 30 within a conduit layer 32 are knitted together with a filament, such as thread, yarn or other suitable material, so as not to substantially or at most only minimally impede and interfere with gas diffusion. This is best illustrated in FIG. 3(*l*), wherein conduits 30 are arranged in a conduit layer 32 and fixed to one another by intermittently knitting one or more filaments along the length of conduit layer 32 to connect adjoining conduits 30.

In an exemplary embodiment, a plurality of conduit layers 32 are stacked on top of one another and oriented parallel to one another in order to form a gas exchange mat 34, as shown in FIGS. 3(*k*) and 3(*m*). Gas exchange mat 34 may be constructed from conduit layers 32 of the same or different dimensions and/or configuration. The length of conduits 30 of two adjoining conduit layers 32 are oriented in the same plane and offset from one another. In one embodiment, the two adjoining conduit layers 32 are oriented substantially perpendicular to one another such that the conduit length of and direction of gas passing through a first conduit layer 32*a* is substantially perpendicular to the conduit length of and direction of gas passing through an adjoining second conduit layer 32*b*. In one embodiment, the conduits 30 of two adjoining conduit layers 32*a*, 32*b* are oriented substantially about 45° to about 135°, about 65° to about 115°, about 75° to about 105°, or about 85° to about 95° out of phase with and relative to one another. By way of example, there may be about 120 to about 160, about 130 to about 155, about 135 to about 153, or about 140 to about 148 conduits layers 32 in gas exchange mat 34. In another embodiment, there may be about 95 to about 115, about 100 to about 108, or about 102 to about 106 conduits layers 32 in gas exchange mat 34. In one embodiment, there may be about 13,119 to about 11,712 conduits 30 in gas exchange mat 34. The resultant gas exchange mat 34 can have any configuration fitted to and/or positionable within blood treatment chamber 24, such as a cuboid or cylinder. This layered arrangement of conduit layers 32 creates a dense network of gas exchange conduits 30 designed to maximize the available surface area for gas transfer and thereby enhance $CO_2$ diffusion efficiency, while still allowing for sufficient flow of blood between the blood inlet and outlet ports 14,16.

Gas exchange module 10 may include one or more gas exchange mats 34. In one embodiment, gas exchange module 10 may have a single gas exchange mat 34. In another embodiment, as best shown in FIG. 3(*g*), two adjacent gas exchange mats 34*a*, 34*b*, each composed of a plurality of stacked conduit layers 32, may be potted within blood treatment component 24. These gas exchange mats 34*a*, 34*b* may adjoin and be positioned in a stacked orientation such that blood passing through blood treatment chamber 24 flows in a direction substantially orthogonal to both gas exchange mats 34. As illustrated in the exemplary embodiment of FIGS. 3(*c*) and 3(*g*), first and second gas exchange mats 34*a*, 34*b* may be spaced apart from one another by a frame 28 having a plurality of openings to allow blood to pass from first gas exchange mat 34*a* to second gas exchange mat 34*b* with no to minimal impedance.

To further improve $CO_2$ diffusion efficiency, the collective thickness of one or more gas exchange mats 34 is may be sufficient to effectively remove in a single pass through the one or more gas exchange mat 34 and/or in a single pass through gas exchange module 10 substantially all the $CO_2$ from the patient's blood that is passed therethrough. A suitable total thickness of the adjoining one or more gas exchange mats 34, identified in the exemplary embodiment of FIG. 3(*j*) as dimension Z, may be described in terms of the length of conduits 30. In one embodiment, the ratio of the active length of conduit 30 to the total thickness of one or more gas exchange mats 34 of gas exchange module 10 may be about 3:1 to about 0.5:1, about 2:1 to about 0.8:1, about 2:1 to about 0.9:1, or about 1:1.1 to about 0.9:1. In another embodiment, the ratio of the active length of conduit 30 to the thickness of gas exchange mat 34 is about 3.5:1 or less; about 3:1 or less, about 2:1 or less, about 1:1 or less or about 1.1:1 or less. In one embodiment, a ratio of about 1:1 suggests that the blood flow path and gas flow path are designed to allow for maximum exposure, processing and filtration of the blood by conduits 30 and to facilitate $CO_2$ diffusion by reducing the relative differences in blood flow and gas flow resistance. In another embodiment, the aforementioned ratio values may also represent the ratio of the active length of conduits 30 to the shortest path of blood flow through the blood treatment chamber. In an exemplary embodiment, the total thickness of the one or more gas exchange mat 34 may have a thickness of about 54.7 mm. In one embodiment, the overall available gas exchange surface area of the gas exchange mat 34 is about 0.5 m$^2$ to about 1.3 m$^2$, 0.5 m$^2$ to about 1.2 m$^2$, about 0.5 m$^2$ to 0.98 m$^2$, or 0.98 m$^2$ to 1.3 m$^2$. The gas exchange mat 34 may include at least about 10,000, at least about 12,000 conduits, at least about 13,000 conduits, at least about 13,119 conduits, or at least about 13,300 conduits. Alternatively or additionally, the gas exchange mat 34 may have at least 13,300 conduits per square meter of gas exchange surface area.

As shown in FIGS. 3(*f*) and 3(*i*)-3(*j*), gas exchange mats 34 are potted within, disposed within, affixed to or otherwise attached to one or more blood treatment chamber 24 positioned within housing internal cavity 13. Blood treatment chamber 24, which is in fluid communication with and connects blood inlet port 14 and blood outlet port 16, is designed to process the blood so as to filter $CO_2$ from the blood circulated through blood treatment chamber 24 by exposure to the gas exchange surface area of one or more gas exchange mats 34, e.g. unpotted surface area of gas exchange mats 34 capable of $CO_2$ diffusion. One or more gas exchange mats 34 may be potted using any suitable material, such as an epoxy resin, within blood treatment chamber 24 so that opposing proximal and distal ends of each conduit layer 32 and the proximal and distal ends 36, 38 of their respective conduits 30 extend across blood treatment chamber 24 and through the walls 26 of blood treatment chamber 24, such that the blood treatment chamber walls 26 form a liquid impermeable and sealed perimeter of the blood treatment chamber 24. The proximal and distal ends 36, 38 of conduits 30 in each conduit layer 32 of gas exchange mat 34 extend outwardly beyond the potted portions of gas exchange mats 34 and blood treatment chamber 24, so as to be in fluid communication with and open to a space exterior to blood treatment chamber 24, namely gas passageways 41*a*, 41*b*. The lumens of conduits 30 are therefore in fluid communication with gas passageways 41*a*, 41*b* as well as gas inlet and outlet ports 18, 20 as described in further detail below.

FIGS. 3(*e*)-3(*f*) and 3(*i*) show a plurality of gas passageways 41*a*, 41*b*, each having two interconnected first and second sections 42*a*, 42*b* and 42*c*, 42*d*, respectively. As shown, gas passageways 41*a*, 41*b* may be configured as channels positioned within the housing internal cavity 13 around and along the perimeter of blood treatment chamber 24. As previously described, gas passageways 41*a*, 41*b* are in fluid communication with conduits 30 for delivering gas to and receiving gas from conduits 30. In the embodiment illustrated in FIG. 3(*i*), each section 42*a*, 42*b*, 42*c*, 42*d*, configured as compartments of gas passageways 41*a*, 41*b*, is defined by a corresponding housing sidewall 22*a*, 22*b*, 22*c*, 22*d* of housing 12 and a corresponding opposing blood treatment chamber wall 26*a*, 26*b*, 26*c*, 26*d* spaced apart relative to one another to form the gas passageways 41*a*, 41*b*. The length of each section 42*a*, 42*b*, 42*c*, 42*d* is oriented in the same plane as and is substantially perpendicular to a length of conduits 30 in fluid communication with the respective sections 42*a*, 42*b*, 42*c*, 42*d*. In one embodiment, all of conduits 30 are in fluid communication with gas inlet port 18 and/or gas outlet port 20 via a gas passageway 41*a*, 41*b*. Gas inlet port 18 may be positioned between and connected to first and second interconnected sections 42*a*, 42*b* of gas passageway 41*a* and is defined by respective adjoining housing sidewalls 22*a*, 22*b* and blood treatment chamber walls 26*a*, 26*b*, forming a forked gas passage. Upon entering gas inlet port 18, gas travels through one of the two diverging sections 42*a*, 42*b* of gas passageway 41*a* and through the proximal ends 36 of conduits 30 of alternating conduit layers 32. For example, gas flowing through section 42*a* passes through a plurality of the alternating conduit layers (i.e. conduit layer 32*a*) in a first direction while gas flowing through section 42*b* passes through adjoining intervening conduit layers (i.e. conduit layer 32*b*) in a second direction perpendicular to the first direction, as illustrated in FIGS. 3(*f*) and 3(*i*). $CO_2$ diffusion occurs upon exposure of and contact between the blood and conduits 30, flowing blood over, around and between the porous membranes of conduits 30 while a gas, such as a gas substantially free of $CO_2$, is flowed through conduits 30. Blood may flow through the interstices of one or more gas exchange mats 34 over, between and around conduits 30 in a direction that is substantially orthogonal to the direction of the gas flow within conduits 30 and substantially orthogonal to a length of conduits 30. Gas exiting a distal end 38 of conduits 30 flow into first and second sections 42*c*, 42*d* of gas passageway 41*b* which converge and deliver the gas to gas outlet port 20. Gas outlet port 20 may be located between and connected to first and second sections 42*c*, 42*d* of gas passageway 41*b*, defined by adjoining housing sidewalls 22*c*, 22*d* and blood treatment chamber walls 26*c*, 26*d*.

In an exemplary embodiment, gas exchange module 10 may optionally further include one or more sensors 44 for detecting a physiological parameter of blood or gas flowing through gas exchange module 10. For example, sensor 44 may be in direct contact with blood entering or exiting gas exchange module 10 and is adapted for detecting and measuring blood pressure, blood flow rate, $CO_2$ content, or $O_2$ content. In the exemplary embodiment shown in FIG. 3(*h*), at least one sensor 44 is located within or otherwise disposed at blood outlet port 16, adjacent to the passageway through which blood flows through blood outlet port 16. A second sensor 44 may also or alternatively be attached to and extend from an internal surface of blood inlet port 14. Optionally, one or more sensors 44 may be in direct contact with gas flowing through gas exchange module 10. For example, sensor 44 may be attached to and/or extend from an internal surface of gas inlet port 18 and/or gas outlet port 20. Each of the above described sensors 44 may be operatively associated with control unit 62 and used to confirm blood flow, blood pressure or $CO_2$ partial pressure within gas exchange module 10; detect the presence of gas or blood leakage through gas exchange module 10; and/or provide information based on which the user may set, change and/or modify the blood and gas flow rates through gas exchange module 10 may be adjusted to achieve efficient or otherwise the desired degree or rate of $CO_2$ diffusion.

Blood treatment system 1 may optionally further include a gas supply unit 50 operatively associated with gas exchange module 10 to provide a continuous stream of gas at a controlled, high velocity flow rate to gas inlet port 18. As shown in FIGS. 1-2, gas supply unit 50 delivers gas directly to gas inlet port 18 of gas exchange module 10 through one or more tubing. In an exemplary embodiment, gas supply unit 50 may be adapted to controls gas flow through conduits 30 such that the gas flow rate through the lumens of conduits 30 is about 0.2 L/min to about 15 L/min, about 1 L/min to about 15 L/min, about 2 L/min to about 15 L/min, or about 5 L/min to about 15 L/min. Gas supply unit 50 may also be used to control the gas pressure within conduits 30. In one embodiment, there is substantially no change in gas pressure across conduit 30.

The gas delivered to conduits 30 may be non-toxic, biocompatible and substantially free from $CO_2$ and may be administered in toxicological safe amounts. In one embodiment, the partial pressure of $CO_2$ in the gas is either negligible or there is no $CO_2$ in the gas. In an exemplary embodiment, the gas may be oxygen, mixtures of oxygen with air, nitrogen or any suitable noble gas. Optionally, gas supply unit 50 may further include one or more gas blending functionalities for mixing or otherwise preparing the gas to be delivered to gas exchange module 10.

Optionally, blood treatment system 1 may further include a blood pump 60 and/or control unit 62 that are operatively associated with gas exchange module 10 for regulating the flow rate of blood through blood treatment chamber 24. In the embodiments shown in FIGS. 2 and 4, blood pump 60 is fluidly connected to a venous access point and gas exchange module through one or more tubing. In one embodiment, pump 60 may be an occlusive (i.e. peristaltic) pump or centrifugal pump, such as the centrifugal pump manufactured by Maquet Cardiopulmonary of Rastatt, Germany and marketed under the trade name ROTASSIST, or a roller pump. A control unit 62 may be integrated in or otherwise operatively associated with pump 60 to regulate blood flow through pump 60 and through blood treatment chamber 24. Pump 60, as instructed by control unit 62, may control and regulate blood flow through gas exchange module 10, specifically through blood treatment chamber 24, at a rate of about 1.2 L/min or less, about 1 L/min or less, about 0.8 L/min or less, about 0.51 L/min or less, about 0.5 L/min or less, about 0.4 L/min to about 0.51 L/min, about 0.4 L/min to about 1 L/min, or about 0.51 L/min to about 1.2 L/min. A user may, as desired, interface with control unit 62 to change the rate of blood flow within a designated low blood flow range.

In an exemplary embodiment, blood treatment system 1 does not have a heat exchanger. In such embodiments, gas exchange module 10 does not have any substantially water impermeable fibers adapted for passing a thermally managed flow of water to heat or cool blood within gas exchange module 10. Additionally, in these embodiments blood treatment system 1 is not designed to provide oxygenation and therefore regulation of blood temperature is not required. Blood treatment system 1 may therefore be configured as a dedicated $CO_2$ removal system adapted specifically and/or only for $CO_2$ diffusion.

Blood treatment system 1 may optionally further includes a catheter providing vascular access to the patient. Since blood treatment system 1 can be operated under conditions of low blood flow, it is possible to work with small-lumen cannulas or dual-lumen cannulas which provide for less invasive vascular access and improved safety, and thus requires fewer monitoring controls and potential complications. In one embodiment, the size of a single lumen cannula may be about 21 French (7 mm) or less, about 13 French (4.33 mm) or less. In another embodiment, the size of a double lumen cannula may be about 24 French (8 mm) or less or about 19 French (6.33 mm) or less. In an embodiment, the size of the single lumen cannula may be selected from those ranging between 21 French to 19 French.

In an exemplary embodiment, the blood contacting lumens (e.g. cannula and tubing lumens), chambers (e.g. blood treatment chamber), components and portions of extracorporeal blood treatment system 1, including those lumens, chambers, compartments and surfaces of gas exchange module 10, optional pump 60, access catheters as well as all connective tubings of system 1 may be coated with a material that improves the biocompatibility of the extracorporeal circulation system and may also be thromboresistant.

While the above described embodiments of blood treatment system 1 describe in particular a $CO_2$ removal system, one skilled in the art would appreciate that blood treatment system 1, gas exchange module 10, particularly conduits 30, and all other described system components may be designed, adapted and configured for the removal, diffusion, extraction or exchange of other gases, in addition to or in place of $CO_2$. In particularly, the gas permeable membrane of conduit 30 and selection of gas to be flowed through conduits 30 may be designed and selected for the transfer of these other gases.

The unique configuration of blood treatment system 1 of the present invention provides numerous operational and therapeutic advantages. Designed to accommodate a low rate of blood flow through gas exchange module 10, the blood treatment system 1 enables the use of minimally invasive small-lumen or dual-lumen cannulas to provide minimally traumatic vascular access. The low blood flow rate also results in low blood pressure conditions within the lumen of conduit 30, which reduces the potential for blood leakage from blood treatment system 1 as well as reduces the severity of the risk associated with blood leakage. Consequently, blood treatment system 1 need not require any or a plurality of highly sensitive, highly restrictive blood pressure and/or blood flow monitors for accessing the possibility of leakages, thereby simplifying the overall system.

Another advantageous feature of the exemplary embodiments of the invention is the configuration and arrangement of gas exchange conduits 30. The relatively short length of conduits 30 decreases fluidic resistance of the gas flowing through conduit 30, which consequently reduces fluidic back-pressure for gases passing through the lumen of conduit 30. The short length of conduit 30 thereby inhibits the formation of microbubbles on an exterior blood contacting surface of the conduit 30 membrane, which can obstruct blood flow in capillaries, cause tissue ischemia and form blood embolisms leading to further vascular and tissue damage. By contrast, oxygenators are designed with long fibers that are few in number in order to achieve mass transfer of gas.

By including a large number of conduits 30 in gas exchange mat 30, no efficiency in the gas exchange module is lost by virtue of the short length of conduits 30. To the contrary, due to the relatively short length of conduits 30 and high gas flow rate therethrough, the difference in the partial pressure of $CO_2$ of the gas and of the patient's blood is greater at the distal end (i.e. gas exiting end) of conduit 30 than a distal end (i.e. gas exiting end) of a longer conduit. Consequently, $CO_2$ diffusion driving force and efficiency is greater as a result of using a plurality of shorter conduits 30.

Additionally, exemplary embodiments of the invention further enhances $CO_2$ removal efficiency by arranging the plurality of parallel conduits 30 in layers 32 to form one or more gas exchange mats 34, such that the conduits 30 of adjoining layers 32 are oriented substantially perpendicular to one another, thereby providing a maximum surface area available for $CO_2$ diffusion. The efficiency of $CO_2$ diffusion is further improved by dictating that the combined thickness of the one or more gas exchange mat 34 is such that the ratio of the active length of a conduit 30 to the total thickness of the one or more gas exchange mats 34 is about 3:1 to about 0.5:1, thereby enabling efficient removal of $CO_2$ from blood flowed through gas exchange module 10 at a low blood low flow rate. In an exemplary embodiment, the thickness of the gas exchange mat may be about 2.6 cm to about 5.4 cm.

Figure 4:
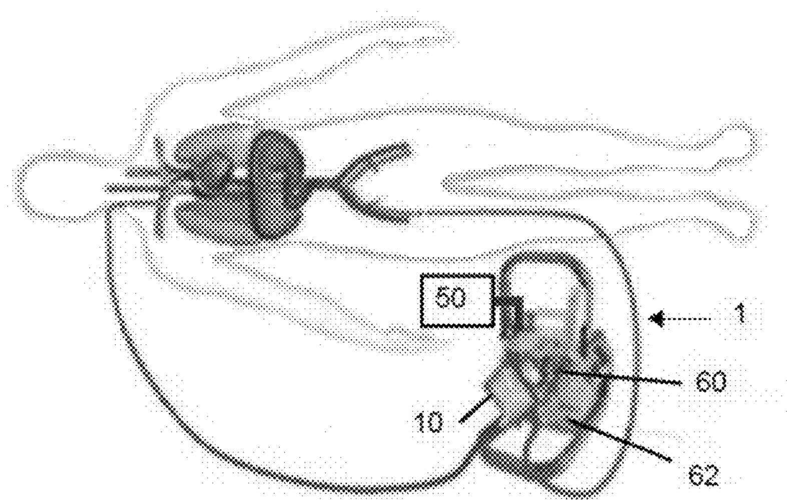
FIG. 4 shows an exemplary blood treatment system attached to a patient's jugular and femoral veins using two small single lumen catheters and including a gas exchange module and integral pump operatively associated with a gas supply unit.
Figure 3A:
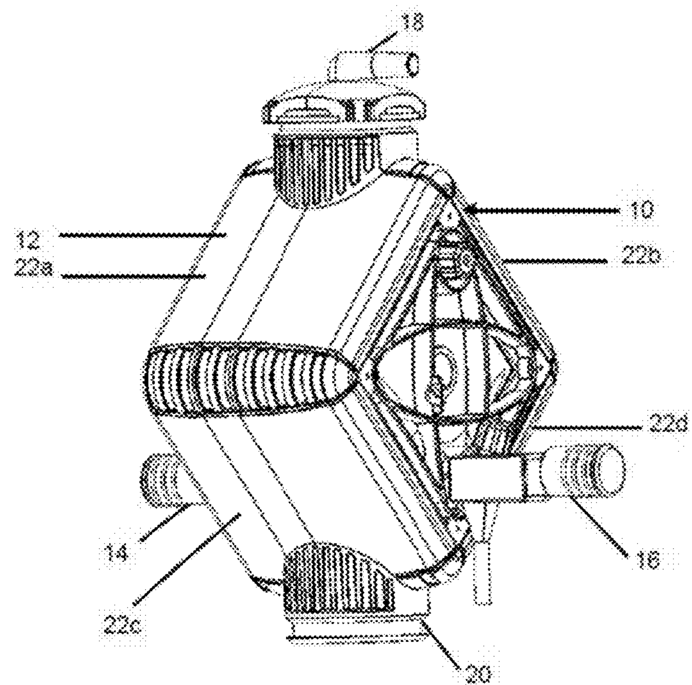
FIG. 3(*a*) is a perspective view of an exemplary gas exchange module of the blood treatment system.
Figure 3B:
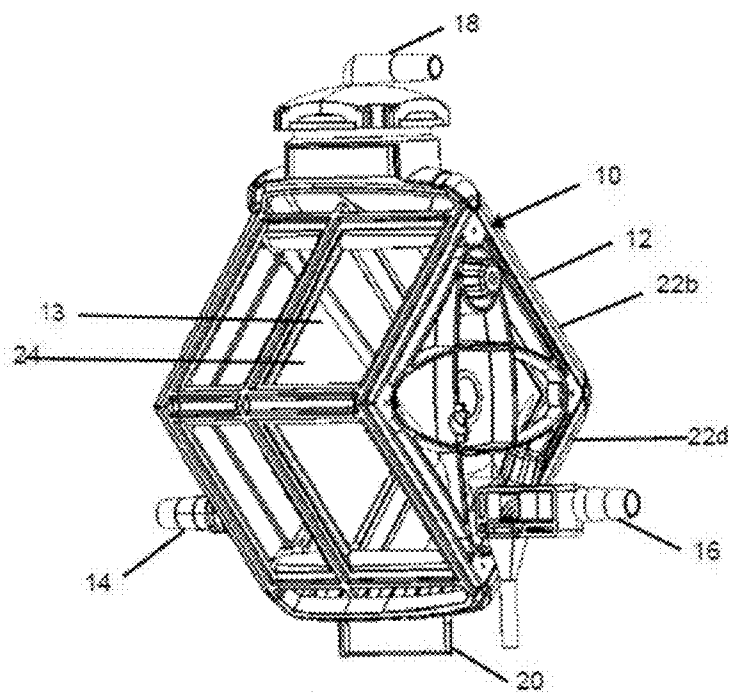
Figure 3C:
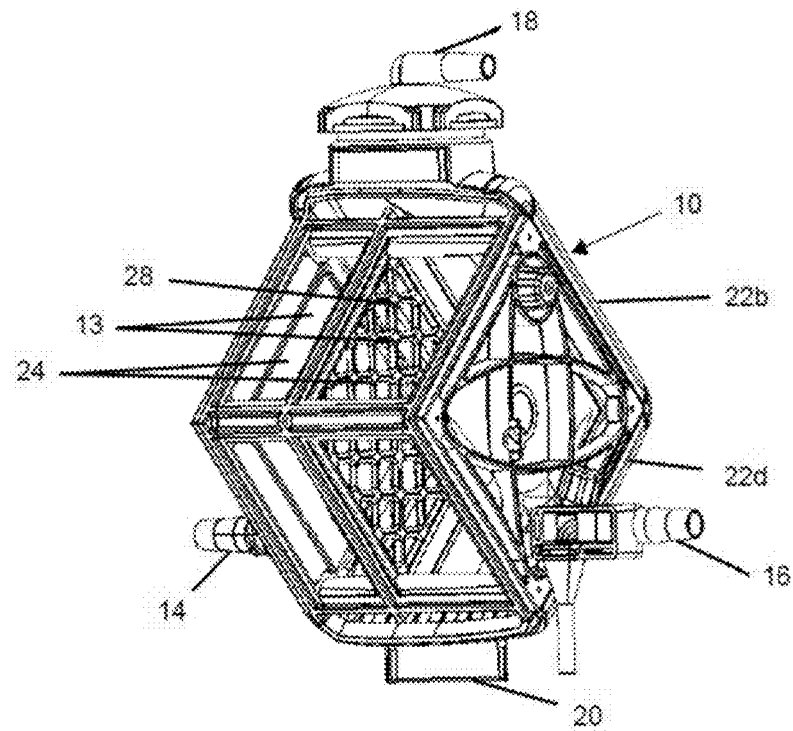
Figure 3D:
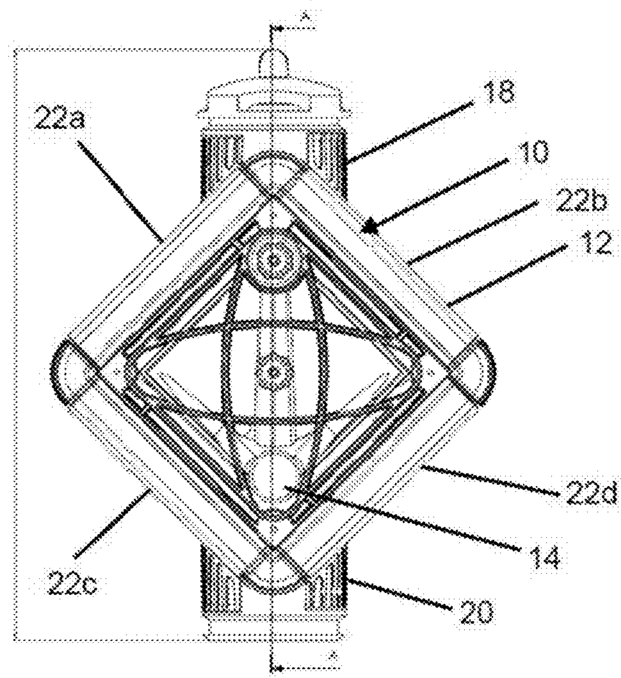
Figure 3E:
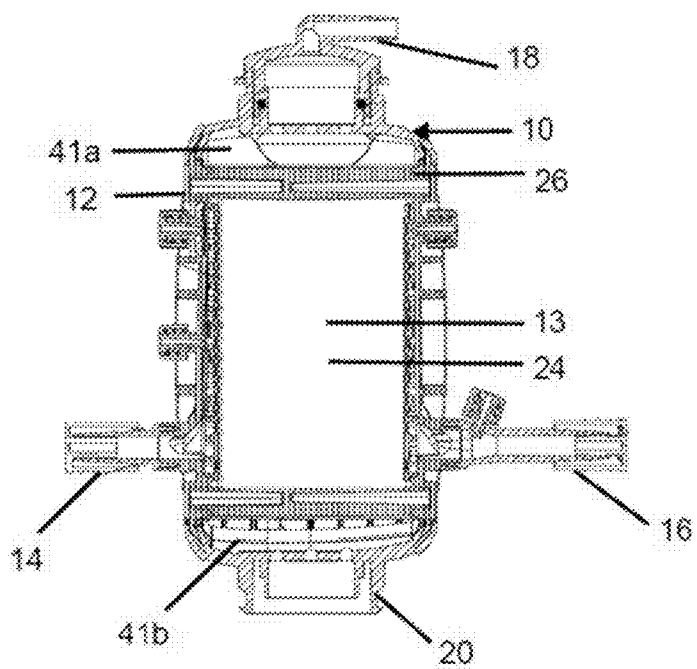
Figure 3F:
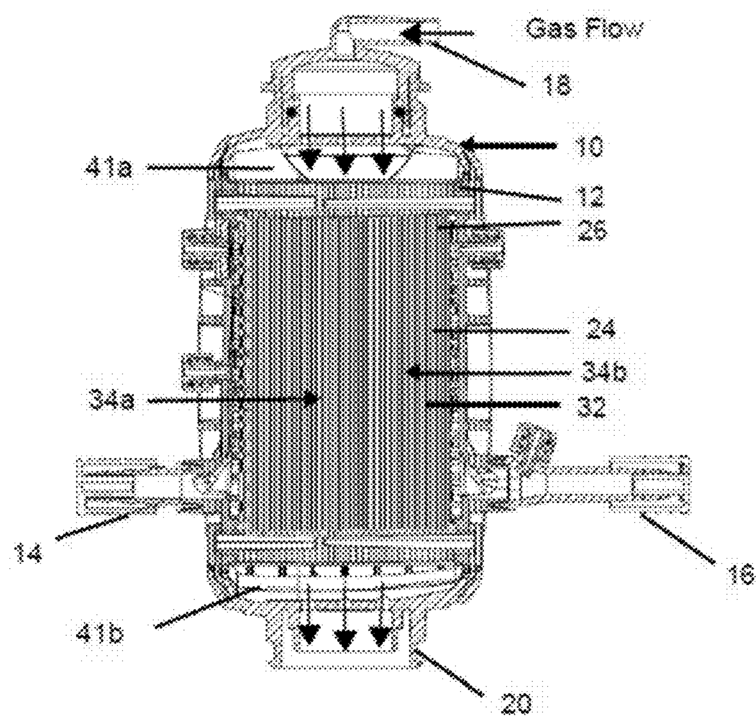
Figure 3G:
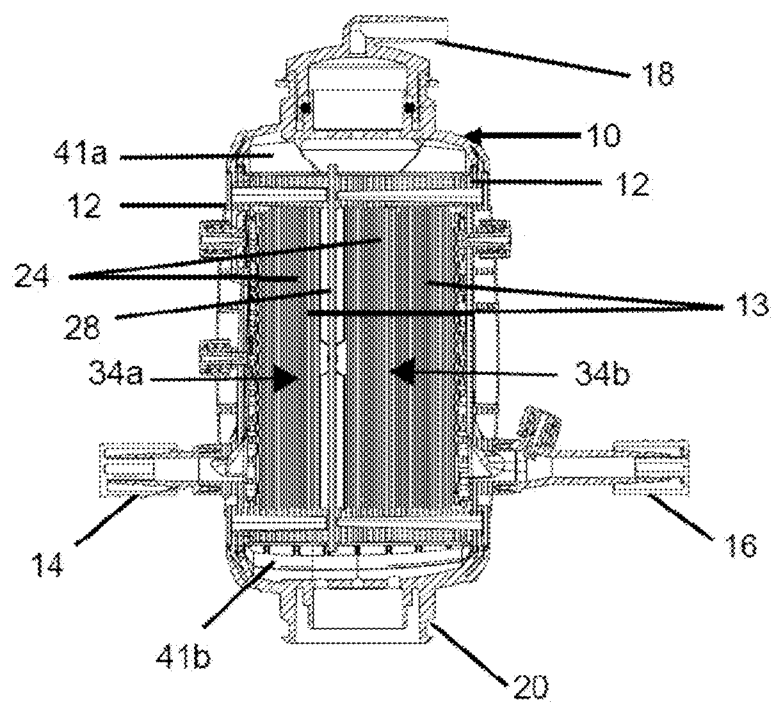
Figure 3H:
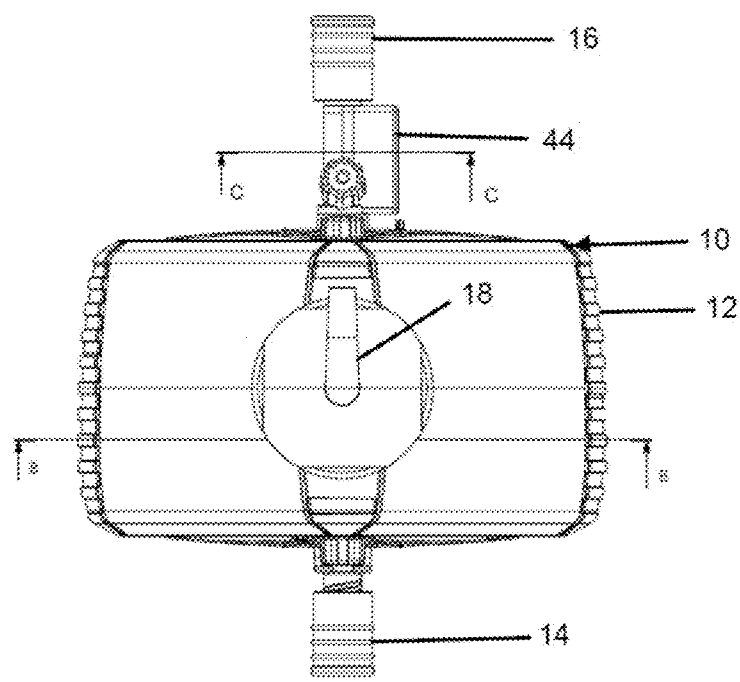
Figure 3I:
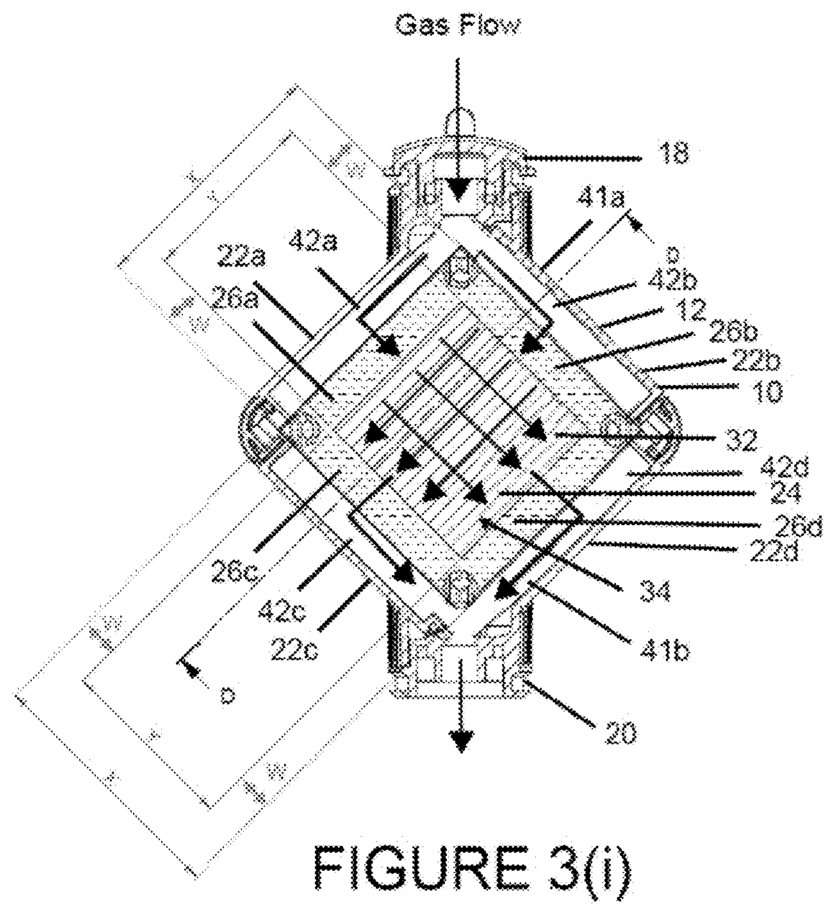
Figure 3J:
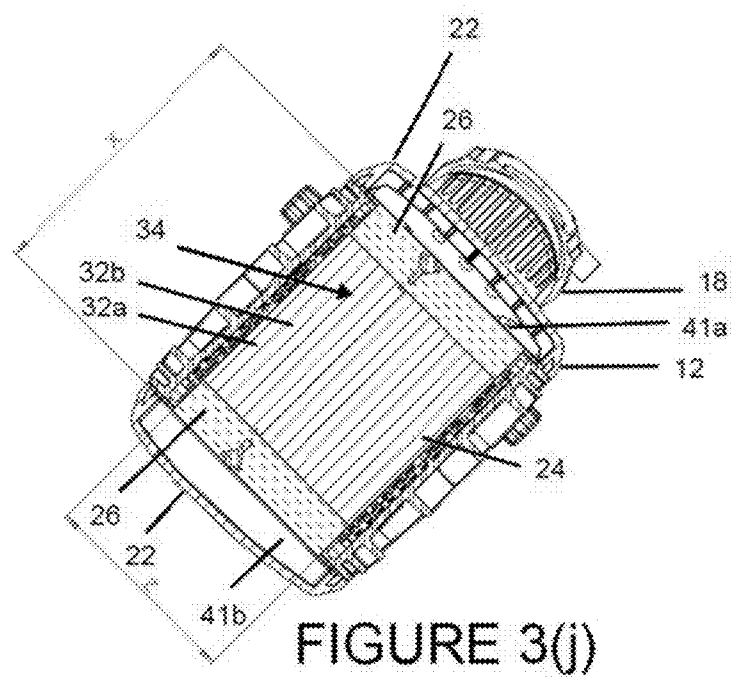
Figure 3K:
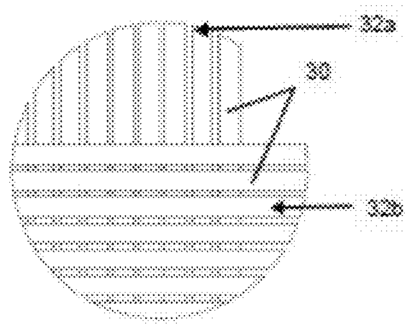
Figure 3L:
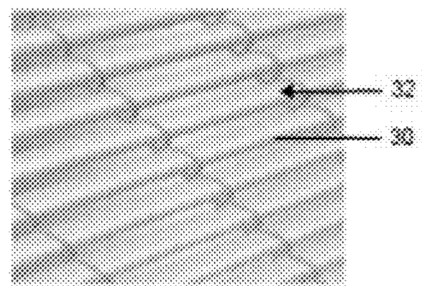
Figure 3M:
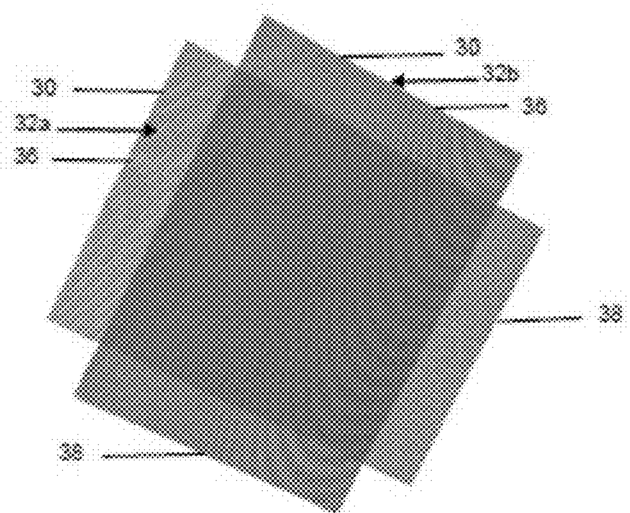
Figure 3N:
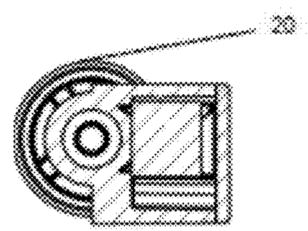

Furthermore, an exemplary embodiment of blood treatment system 1 and all its components, including gas exchange module 10 may be compact, light-weight and portable, enabling a patient to remain mobile while being treated. In one embodiment, the various components of system 1 may be integrated into a single device that is either hand-held or otherwise portable, as shown in FIGS. 1-2 and 4. In one embodiment, all the components of system 1 may be removably positioned on, hung on or otherwise attached to a wheeled cart or stand, enabling a patient to easily roll system 1 to a desired location with minimal hindrance, thereby allowing system 1 to move with the patient.

Blood Treatment Method

The present invention is further directed to a novel method for removing $CO_2$ from blood circulated through extracorporeal blood treatment system 1. In one embodiment, the method involves accessing a patient's circulatory system, directing blood through a circuit of the extracorporeal blood treatment system so as to remove substantially all the $CO_2$ from the blood upon passage through gas exchange module 10 and returning the substantially $CO_2$ free blood to the patient's circulatory system. This therapeutic method may be used to treat a variety of respiratory conditions associated with impaired lung functionality, particularly health problems associated with excess $CO_2$ concentration in the blood or inhibited ability to remove $CO_2$ from the blood. Exemplary conditions that may be treated with the present method include diseases, syndromes, injuries or defects affecting lung function including but not limited to COPD, chronic and acute hypercapnia, respiratory acidosis, ALI and ARDS.

Figure 5:
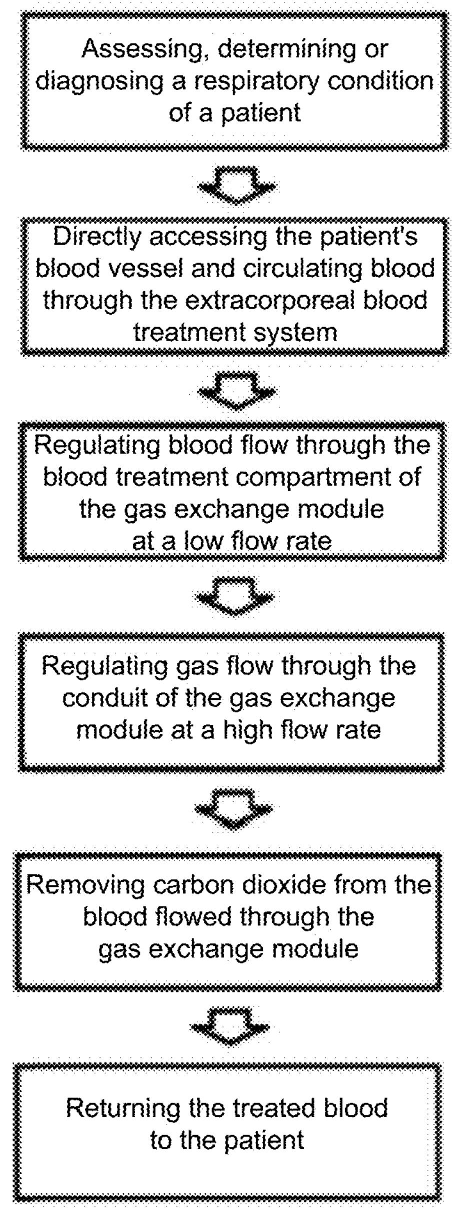
FIG. 5 shows a flow chart of describing an exemplary blood treatment method of the present invention.

In the exemplary embodiment set forth in FIG. 5, the method involves diagnosing a patient with or otherwise accessing/determining the likelihood that a patient has a respiratory condition and applying the blood treatment system 1 to the patient for the purpose of decreasing $CO_2$ concentration in a patient's blood or otherwise treating the respiratory condition. In particular, a physician may select and apply any one of the aforementioned embodiments of blood treatment system 1, including any gas exchange module 10, optional gas supply unit 50, optional pump 60, or combinations thereof that is adapted for treating a patient, in particular for treating an adult human. The physician may also select the gas flow, blood flow and/or the gas to be delivered to the conduits in order to optimize $CO_2$ diffusion. In one embodiment, the parameters set by the physician for gas flow, blood flow and/or gas selection are not optimized for transfer of $O_2$ for patient oxygenation.

Vascular access is achieved by percutaneous cannulation of the jugular vein, subclavian vein, femoral vein or any combinations thereof using two small single lumen catheters or a double lumen catheter. The tip of the catheter or a separate needle positioned within a cannula of the catheter may be used to create a small vascular puncture site, connecting the catheter to the patient's circulatory system. When using a needle, upon puncture, the needle may be retracted and/or the catheter may be advanced to secure the catheter to the vein. In an exemplary embodiment, only a single puncture site is necessary to provide vascular access, such as venous-venous access using a small double lumen catheter.

A tubing attached to a proximal port of the catheter may be used to transport blood from the vascular access site to and from gas exchange module 10 at a low flow rate. In exemplary embodiments of blood treatment system 1 that include optional pump 60, blood is transported to pump 60 which directs and delivers the blood to blood treatment chamber 24 of gas exchange module 10 at a controlled rate. Control unit 62, operatively associated with pump 60, instructs pump 60 to regulate blood flow through blood treatment chamber 24 at a predetermined low flow rate. If desired, the user may instruct controller 62 and/or pump 60 to change the rate of blood flow through gas exchange module 10 within a designated low flow rate range. In one embodiment, blood is delivered to blood inlet port 14 and through blood treatment chamber 24 at a positive, non-zero low flow rate, such as about 0.5 L/min or less.

As blood is delivered to gas exchange module 10, optional gas supply unit 50 supplies a continuous stream of gas substantially free of $CO_2$ to gas inlet port 18 of gas exchange module 10. Best shown in FIGS. 3(*f*) and 3(*i*), gas flows through gas inlet port 18 and diverges into one of two compartments or sections 42*a*, 42*b* of gas passageway 41*a* which are in fluid communication with open conduit ends of the conduits 30 of alternating conduit layers 32 that form gas exchange mat 34. The gas then flows through the conduits 30 of respective conduit layers 32 in a direction substantially perpendicular to the length of the corresponding sections 42*a*, 42*b*, as illustrated by the arrows in FIG. 3(*i*). In one embodiment, gas supply unit 50 controls and regulates the flow rate of gas such that the gas flow rate through conduits 30 is maintained at a high velocity of about 15 L/min. Additionally, the gas pressure within conduits 30 may be kept low and regulated so that it does not exceed a level at which conditions would induce microbubble formation, i.e. bubble point.

When blood enters blood inlet port 14 and flows into blood treatment chamber 24, the flow of blood is oriented in a direction substantially orthogonal to the one or more gas exchange mats 34, conduit layers 32 and the respective lengths of conduits 30. Blood passes through the interstices of and contacts the one or more gas exchange mats 34 so as to pass over, around and between the exterior surface of individual conduits 30 forming conduit layers 32 and one or more gas exchange mats 34. Upon contact with and exposing the flow of blood to the porous membrane of conduits 30, through which a constant supply of gas substantially free of $CO_2$ is flowed, $CO_2$ diffuses from the blood, through the porous membrane of conduit 30 and is swept along and through the lumen of conduit 30 by the high velocity gas flowing through conduit 30. The difference in the partial pressure of $CO_2$ in the patient's blood introduced into gas exchange module 10 and any partial pressure of $CO_2$ in the gas circulated through conduits 30 drives the diffusion of $CO_2$ from the blood and into the lumen of conduit 30. In an exemplary embodiment, this difference in the partial pressure of $CO_2$ may be about 45 mm Hg to about 70 mm Hg, about 45 mm Hg to about 50 mm Hg, or about 40 mm Hg to about 50 mm Hg. By providing a high velocity stream of gas through conduit 30, the exposure and contact time between the blood and gas flowing through conduits 30 is relatively short. Consequently, the partial pressure of $CO_2$ in the blood and the partial pressure of $CO_2$ in the gas, or lack thereof, is prevented from equilibrating, thereby maintaining a continuous driving force of $CO_2$ diffusion created by the blood and gas $CO_2$ partial pressure differential. The gradient of the high $pCO_2$ concentration in blood in comparison to the low $pCO_2$ gradient in the gas is therefore maintained by the high velocity of gas flowing through conduits 30; gas carrying diffused $CO_2$ from blood is quickly purged and replaced with new gas having substantially no $CO_2$. The gradient is further maintained as only small amounts of $pCO_2$ are diffused from the blood and into each conduit lumens. As discussed above, near complete removal of $pCO_2$ from the blood, however, may be accomplished by including a plurality of such short conduits 30 within gas exchange mat 34.

In an exemplary embodiment, substantially all the $CO_2$ may be removed from the blood introduced into gas exchange module 10 upon a single pass of the blood through gas exchange module 10, specifically through blood treatment chamber 24 and gas exchange mats 34. In one embodiment, the percent of $CO_2$ removed from blood after a single pass through gas exchange module 10 may be about 10% to about 95%, about 20% to about 90%, about 40% to about 90%, and 60% to about 90%. The partial pressure of $CO_2$ in the blood after a single pass through the gas exchange module 10 may be about 60 mm Hg to about 5 mm Hg, about 40 mm Hg or less, about 30 mm Hg to about 10 mm Hg, or about 25 mm Hg to about 5 mm Hg. In an exemplary embodiment, the pH of blood after a single pass through gas exchange module 10 may be about 7.45 or more, about 7.6 or more, about 7.8 or more, about 7.5 to about 8.2, about 7.6 to about 8.2, or about 7.7 to about 8.2.

A fresh supply of gas may be constantly streamed through gas exchange module 10, and the patient's blood may be recirculated through extracorporeal blood treatment system 1 as desired until all or substantially all the $CO_2$ is removed. In an exemplary embodiment, the method of the present invention allows for the complete or substantially complete depletion of all $CO_2$ from the treated blood.

The gas containing $CO_2$ leaving conduits 30 is collected in first and second sections 42*c*, 42*d* of gas passageway 41*b* and pushed out through gas outlet port 20 of gas exchange module 10 by the high velocity flow of gas in gas passageways 41*a*, 41*b* and conduits 30. This gas may be subsequently vented to atmosphere or collected in a reservoir. In one embodiment, gas outlet port 20 may optionally connected to a vacuum source to further control the rate of gas flow through conduits 30.

The overall duration of the therapy may be up to about 30 days, about 6 hours to about 30 days. In another embodiment, the therapy may last for a period of time up to about 5 days or about 6 hours to about 5 days. Additionally, the therapy may be continuously or intermittently administered as needed to achieve the desired degree of $CO_2$ removal.

The same or similar method of use of other embodiments blood treatment system 1 may be used to remove, extract, transfer or exchange other gases from the blood. Again, blood treatment system 1, inclusive of gas exchange module 10, particularly conduits 30 and the selection of gas to be flowed through conduits 30, as well as all other described system components may be designed, adapted and configured for the removal, diffusion, extraction or exchange of other gases in addition to or in place of $CO_2$.

The $CO_2$ removal method of the present invention has a number of therapeutic advantages. For example, low blood flow makes it possible to decrease the invasiveness of the procedure by reducing the size of the vascular access point, permitting usage of a small-lumen or small dual-lumen cannulas which causes less stress and trauma to the vessels during cannulation. Moreover, the veno-venous cannulation, low blood flow and corresponding low blood pressure reduces the risk of death or consequences associated with the patient bleeding out due to blood leakage from blood treatment system 1.

Additionally, the high velocity stream of gas through conduits 30 maintains a stable and maximized driving force of $CO_2$ diffusion created by the difference in the $CO_2$ partial pressure of the patient's blood and in the gas. Microbubble formation on the blood contacting outer surface of the conduit 30 membrane is also inhibited by maintaining a low gas pressure in conduits 30.

Furthermore, in one embodiment, the method enables efficient $CO_2$ diffusion by endeavoring to substantially remove all $CO_2$ from blood in a single pass through gas exchange module 10 and seeking to achieve non-physiological values of the partial pressure of $CO_2$ in blood and non-physiological values of blood pH. For example, the $pCO_2$ of the treated arterial blood may be about 32 mm Hg or less, about 25 mm Hg or less, about 15 mm Hg or less, and the pH of treated arterial blood may be about 7.45 or more, about 7.6 or more, or about 7.8 or more, representative of respiratory alkalosis. In one embodiment, the $pCO_2$ value of the treated arterial blood may be about 10 to about 15 mm Hg and the pH value may be about 7.8. In one embodiment, the $pCO_2$ value of the treated arterial blood may be about 10 mmHg to about 32 mm Hg and the pH value may be about 7.45 to about 7.8. In these embodiments, the method may involve targeting and managing therapy conditions to these atypical values that are not within standard acceptable physiological ranges. In contrast, oxygenators are optimized to maintain normal physiological partial pressures of gas, inclusive of $CO_2$; mass transfer of gas is thus only achievable by requiring a high blood flow through the oxygenator and complete elimination of $CO_2$ would not be possible. Surprisingly, the blood treatment system 1 of the present invention is as or more effective than large gas exchange modules that require high blood flow and whose gas exchange conduits have greater gas exchange surface areas.

EXAMPLES

Example 1

In one embodiment, gas exchange module 10 of the present invention has the same configuration as shown in FIGS. 3(*a*)-3(*b*), 3(*d*)-3(*f*) and 3(*h*)-3(*m*). Gas exchange module 10 included a gas exchange mat 34 constructed from 13,834 or more microporous gas permeable conduits 30 adapted for carbon dioxide diffusion. Conduits 30 were positioned parallel to one another to form conduit layers 32. The conduit layers 32 were stacked on top of one another to form gas exchange mat 34, each layer oriented perpendicular to an adjoining layer. All of the conduits 30 had an active length of about 5.5 cm and a total conduit length of about 7.6 cm. The active length percentage of conduit 30 capable of gas transfer was at most about 72.4%. Gas exchange mat 34 had a total gas exchange surface area of about 0.98 $m^2$ and a conduit density of about 14,116 conduits per $m^2$. The ratio of a maximum conduit active length to the 5.4 cm thickness of the gas exchange mat 34 (which can also be expressed here as the minimum distance of the blood flow passageway through blood treatment chamber 24) is about 1.02:1. The blood and gas flow paths through gas exchange mat 34 and blood treatment chamber 24 were designed to expose the blood to conduits 30 and ensure comprehensive treatment and processing of the blood passing therethrough. This configuration also facilitates $CO_2$ diffusion by virtue of the relative blood flow resistance and gas flow resistance.

Example 2

In one embodiment, gas exchange module 10 of the present invention has the same configuration as shown in FIGS. 3(*a*)-3(*b*), 3(*d*)-3(*f*) and 3(*h*)-3(*m*). Gas exchange module 10 included a gas exchange mat 34 constructed from 13,119 or more microporous gas permeable conduits 30 adapted for carbon dioxide diffusion. Conduits 30 were positioned parallel to one another to form conduit layers 32. The conduit layers 32 were stacked on top of one another to form gas exchange mat 34, each layer oriented perpendicular to an adjoining layer. All of the conduits 30 had an active length of about 5.8 cm and a total conduit length of about 7.6 cm. The active length percentage of conduit 30 capable of gas transfer was at most about 76.3%. Gas exchange mat 34 had a total gas exchange surface area of about 0.98 $m^2$ and a conduit density of about 13,300 conduits per $m^2$. The ratio of a maximum conduit active length to the 5.4 cm thickness of the gas exchange mat 34 (which can also be expressed here as the minimum distance of the blood flow passageway through blood treatment chamber 24) is about 1.07:1. The blood and gas flow paths through gas exchange mat 34 and blood treatment chamber 24 were designed to expose the blood to conduits 30 and ensure comprehensive treatment and processing of the blood passing therethrough. This configuration also facilitates $CO_2$ diffusion by virtue of the relative blood flow resistance and gas flow resistance.

Example 3

In one embodiment, gas exchange module 10 of the present invention has the same configuration as shown in FIGS. 3(*a*)-3(*b*), 3(*d*)-3(*f*) and 3(*h*)-3(*m*). Gas exchange module 10 included a gas exchange mat 34 constructed from 17,148 or more microporous gas permeable conduits 30 having an outer diameter of about 0.35 mm and is adapted for carbon dioxide diffusion. Conduits 30 were positioned parallel to one another to form conduit layers 32. The conduit layers 32 were stacked on top of one another to form gas exchange mat 34, each layer oriented perpendicular to an adjoining layer. All of the conduits 30 had an active length of about 5.2 cm and a total conduit length of about 7.6 cm. The active length percentage of conduit 30 capable of gas transfer was at most about 68.4%. Gas exchange mat 34 had a total gas exchange surface area of about 0.98 $m^2$ and a conduit density of about 17,497 conduits per $m^2$. The ratio of a maximum conduit active length to the 5.4 cm thickness of the gas exchange mat 34 (which can also be expressed here as the minimum distance of the blood flow passageway through blood treatment chamber 24) is about 0.963:1. The blood and gas flow paths through gas exchange mat 34 and blood treatment chamber 24 were designed to expose the blood to conduits 30 and ensure comprehensive treatment and processing of the blood passing therethrough. This configuration also facilitates $CO_2$ diffusion by virtue of the relative blood flow resistance and gas flow resistance.

The foregoing description of the invention has been presented for the purpose of illustration and description only and is not to be construed as limiting the scope of the invention in any way. The scope of the invention is to be determined from the claims appended hereto.

The invention claimed is:

1. An extracorporeal blood treatment system comprising:

a gas exchange module configured to provide a passageway for blood and to remove substantially all carbon dioxide from the blood as the blood passes through the gas exchange module, wherein the gas exchange module comprises a plurality of conduits that comprise pores forming a plurality of conduit layers that form one or more gas exchange mats, wherein conduits within each conduit layer are arranged in parallel to one another and conduits of adjoining conduit layers are arranged substantially perpendicular to those conduits of the adjoining layers, wherein at least one conduit of each conduit layer is configured to provide a passageway for gas and to allow along a first length of the at least one conduit diffusion of carbon dioxide from the blood upon exposure of the blood to an exterior surface of the at least one conduit, wherein a ratio of the first length to a total thickness of the gas exchange mats is about 1:1 to about 0.5:1; and wherein the extracorporeal blood treatment system does not have a heat exchange mechanism.

2. The system of claim 1, wherein a collective average of the first lengths of the conduits that comprise pores is about 5.8 cm or less.

3. The system of claim 1, wherein the at least one of the plurality of conduits has an outer diameter of about 350 μm to about 410 μm, or all of the conduits that comprise pores have an average outer diameter of about 350 μm to about 410 μm.

4. The system of claim 1, wherein a first length of the at least one of the conduits that comprise pores is about 76.3% or less than a full length of the at least one of the conduits that comprise pores, or an average of the first lengths of all of the conduits that comprise pores is about 76.3% or less than an average of the full length of all of the conduits that comprise pores.

5. The system of claim 1, wherein the pores of the conduits that comprise pores are about 0.2 microns or less.

6. The system of claim 1, wherein the at least one conduit has a microporous microstructure covered by a thick and impervious diffusion layer membrane.

7. The system of claim 1, wherein the conduits that comprise pores are arranged as conduit layers located between a blood inlet and a blood outlet of the gas exchange module, the blood inlet faces these conduit layers so that blood flows towards these conduit layers in a direction substantially orthogonal to the conduits that comprise pores.

8. The system of claim 7, wherein each conduit layer is comprised of conduits that comprise pores arranged substantially parallel to one another and knitted or woven together by a separate thread or thread-like structure.

9. The system of claim 1, wherein the gas exchange module comprises at least 10,000 conduits that comprise pores.

10. The system of claim 1, wherein the system further comprises a pump operatively associated with the gas exchange module for directing and regulating a flow of the blood to the gas exchange module, wherein the pump is adapted to deliver the blood to the gas exchange module at a rate between about 0.2 L/min to about 0.8 L/min.

11. The system of claim 1, wherein the gas exchange module comprises a pressure sensor in direct contact with the blood exposed to the conduits that comprise pores for measuring blood pressure as the blood exits the gas exchange module.

12. The system of claim 1, wherein the gas exchange module further comprises a gas inlet and gas outlet, wherein all of the conduits of the gas exchange module that comprise pores are in fluid communication with the gas inlet.

13. The system of claim 1, wherein the system does not regulate the temperature of any fluid entering the gas exchange module through any inlet including the gas inlet.

14. The system of claim 1, wherein the system further comprises a cannula operatively associated with the gas exchange system, wherein the cannula has a size of about 20 French (6.7 mm) or less.

15. An extracorporeal blood treatment system comprising:

a gas exchange module configured to provide a passageway for blood and to remove substantially all carbon dioxide from the blood as the blood passes through the gas exchange module, wherein the gas exchange module comprises a plurality of conduits, at least one conduit is configured to provide a passageway for gas and to allow for diffusion of carbon dioxide from the blood through a wall of the at least one conduit and to the passageway upon exposure of the blood to an exterior surface of the at least one conduit, wherein the at least one conduit has a first length available for carbon dioxide diffusion of about 5.8 centimeters or less, and wherein percentage of the first length to overall length of the at least one conduit is about 40% to about 76.3%; and wherein the extracorporeal blood treatment system does not have a heat exchanger adapted for regulating the temperature of the blood.

16. An extracorporeal blood treatment system comprising:

a gas exchange module configured to provide a passageway for blood and to remove 60% to about 95% of the carbon dioxide from the blood as the blood passes through the gas exchange module, wherein the gas exchange module comprises:

a plurality of conduits, at least one conduit is configured to provide a passageway for gas and to allow for diffusion of carbon dioxide from the blood upon exposure of the blood to an exterior surface of the at least one conduit, wherein the at least one conduit has a first length available for carbon dioxide diffusion of about 5.8 centimeters or less; and a gas inlet and gas outlet, wherein all of the conduits of the gas exchange module are operatively associated with the gas inlet to permit fluid communication of the gas though the gas exchange module so that gas flowing through the gas exchange module is substantially orthogonal to the blood flow through the gas exchange module.

17. A method for using a blood treatment system to remove carbon dioxide from blood, wherein the blood treatment system is an extracorporeal blood treatment system according to claim 1, and wherein the method for using the blood treatment system comprises the steps of:

selecting a gas then delivering the gas to the plurality of conduits that comprise pores of the gas exchange module of the extracorporeal blood treatment system to treat an adult human;

flowing the blood into the gas exchange module at a rate of 1 liter per minute or less; and exposing the blood to the plurality of conduits that comprise pores to remove carbon dioxide from the blood.

18. The method of claim 17, wherein the blood flows into the gas exchange module at a rate of 0.51 liters per minute or less.

19. The system of claim 1, wherein the conduits that comprise pores are made of polymethylpentene.

* * * * *